US011016094B2

(12) United States Patent
Gilboa-Geffen

(10) Patent No.: US 11,016,094 B2
(45) Date of Patent: *May 25, 2021

(54) COMPOSITIONS AND METHODS FOR ALLERGEN DETECTION

(71) Applicant: DOTS Technology Corp., Natick, MA (US)

(72) Inventor: Adi Gilboa-Geffen, Wayland, MA (US)

(73) Assignee: DOTS TECHNOLOGY CORP., Natick, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/575,440

(22) Filed: Sep. 19, 2019

(65) Prior Publication Data

US 2020/0018764 A1 Jan. 16, 2020

Related U.S. Application Data

(63) Continuation of application No. 15/569,808, filed as application No. PCT/US2016/029356 on Apr. 26, 2016, now Pat. No. 10,466,246.

(60) Provisional application No. 62/154,200, filed on Apr. 29, 2015.

(51) Int. Cl.

| G01N 33/58 | (2006.01) |
|---|---|
| G01N 33/542 | (2006.01) |
| A61K 38/00 | (2006.01) |
| G01N 33/53 | (2006.01) |
| G01N 33/68 | (2006.01) |
| C12M 1/34 | (2006.01) |
| A61P 37/00 | (2006.01) |

(52) U.S. Cl.
CPC .......... *G01N 33/582* (2013.01); *A61K 38/00* (2013.01); *C12M 1/34* (2013.01); *G01N 33/5308* (2013.01); *G01N 33/542* (2013.01); *G01N 33/68* (2013.01); *A61P 37/00* (2018.01); *C12N 2310/16* (2013.01); *G01N 2800/24* (2013.01)

(58) Field of Classification Search
CPC ... G01N 33/582; A61K 38/00; C12N 2310/16
See application file for complete search history.

(56) References Cited

U.S. PATENT DOCUMENTS

| 6,680,377 | B1 | 1/2004 | Stanton et al. | |
|---|---|---|---|---|
| 8,071,734 | B2 | 12/2011 | Stanton et al. | |
| 10,344,319 | B2* | 7/2019 | Gilboa-Geffen | ..... C12Q 1/6811 |
| 10,466,246 | B2* | 11/2019 | Gilboa-Geffen | ....... G01N 33/68 |
| 2004/0038307 | A1 | 2/2004 | Lee et al. | |
| 2005/0238535 | A1 | 10/2005 | Knezevic et al. | |
| 2007/0111222 | A1 | 5/2007 | Chasin et al. | |
| 2008/0044834 | A1 | 2/2008 | Heyduk | |
| 2012/0040865 | A1 | 2/2012 | Kim | |

FOREIGN PATENT DOCUMENTS

| CN | 1742201 A | 3/2006 |
|---|---|---|
| CN | 102083848 A | 6/2011 |
| CN | 103048449 A | 4/2013 |
| JP | 2016536018 | 11/2016 |
| WO | 2004046687 A2 | 6/2004 |
| WO | 2005051174 A2 | 6/2005 |
| WO | 2010001074 A2 | 1/2010 |
| WO | 2013178844 A1 | 12/2013 |
| WO | 2015066027 A2 | 5/2015 |

OTHER PUBLICATIONS

Canadian Office Action dated Sep. 24, 2019 in Application No. 2983307, entitled: Compositions and Methods for Allergen Detection.
International Search Report and Written Opinion dated Oct. 7, 2016 in Application No. PCTUS2016029356, entitled: Compositions and Methods for Allergen Detection.
GenBank Accession No. CL010291 ZMMBBb0553H07rZMMBBb (Hindlll) Zea mays subsp. mays genomic clone ZMMBBb0553H07 3-, genomic survey sequence Dec. 29, 2003 http://www.ncbi.nlm.nih.gov/nucgss/40371569/>. whole doc.
Amaya-González, S. et al. (2013) Aptamer-Based Analysis: A Promising Alternative for Food Safety Control, Sensors 2013, 13, 16292-16311; doi:10.3390/s131216292.
Hall, B. et al. (2009) Kinetic Optimization of a Protein-Responsive Aptamer Beacon, Biotechnology and Bioengineering, vol. 103, No. 6, Aug. 15, 2009.
Hamaguchi, N, et al. (2001) Aptamer Beacons for the Direct Detection of Proteins, Analytical Biochemistry 294, 126-131.
Nadal, P., et al.(2012) DNA Aptamers against the Lup an 1 Food Allergen, PLoS ONE 7(4): e35253. doi:10.1371/ journal.pone. 0035253.
Nadal, P. et al. (2013) Probing high-affinity 11-mer DNA aptamer against Lup an 1 (b-conglutin), Springer-Verlag Berlin Heidelberg 405:9343-9349.
Tan, L., et al. (2005) Molecular beacons for bioanalytical applications, The Analyst, 2005, 130, 1002-1005.
Tran, D.T., et al. (2010) Selection and Characterization of DNA Aptamers for Egg White Lysozyme, Molecules 2010, 15, 1127-1140.
Tran, D.T., et al. (2013) Selection of aptamers against Ara h 1 protein for FO-SPR biosensing of peanut allergens in food matrices, Biosensors and Bioelectronics 43 (2013) 245-251.
Tuleuova, N., et al. (2010), Micropatterning of Aptamer Beacons to Create Cytokine-Sensing Surfaces, Cellular and Molecular Bioengineering, vol. 3, No. 4, Dec. 2010, pp. 337-344.
Wang, H., et al. (2011) Fluorescence protection assay: a novel homogeneous assay platform toward development of aptamer sensors for protein detection, Nucleic Acids Research, 2011, vol. 39, No. 18 e122.

(Continued)

Primary Examiner — Brian Whiteman
(74) Attorney, Agent, or Firm — DT Ward, PC; Donna T. Ward; Lingyun Jia

(57) ABSTRACT

The present invention is drawn to nucleic acid aptamer based signaling polynucleotides (SPNs) for allergen detection in samples. Disclosed herein include compositions, compounds, assays and methods of using said SPNs to detect one or more allergens in a sample, particularly food allergens in a food product.

7 Claims, 3 Drawing Sheets

Specification includes a Sequence Listing.

(56) References Cited

OTHER PUBLICATIONS

Canadian Office Action dated Jun. 7, 2018 in Application No. 2983307, entitled: Compositions and Methods for Allergen Detection.
Australian Examination Report 1 dated Aug. 31, 2018 in Application No. 2016256391, entitled: Compositions and Methods for Allergen Detection.
Partial Supplementary European Search Report dated Sep. 19, 2018 in Application No. 16786996.5, entitled: Compositions and Methods for Allergen Detection.
T. Mairal et al. "FRET-based dimeric aptamer probe for selective and sensitive Lup an 1 allergen detection", Biosensors and Bioelectronics, vol. 54, Nov. 7, 2013 (Nov. 7, 2013), pp. 207-210.
Nutiu et al. "Aptamers with fluorescence-signaling properties", MET, Academic Press, US, vol. 37, No. 1, Sep. 1, 2005 (Sep. 1, 2005), pp. 16-25.
Japanese Office Action dated Oct. 2, 2018 in Application No. 2017-556607, entitled:Compositions and Methods for Allergen Detection and English translation.
Sonia Amaya-Gonzalez, et al., "Affinity of aptamers binding 33-mer gliadin peptide and gluten proteins: Influence of immobilization and labeling tags," Analytica Chimica Acta, 2015, vol. 873, p. 63-70, published online on Feb. 20, 2015.
Extended European Search Report dated Dec. 21, 2018 in Application No. 16786996.5, entitled: Compositions and Methods for Allergen Detection.
Australian Examination Report 2 dated Mar. 15, 2019 in Application No. 2016256391, entitled: Compositions and Methods for Allergen Detection.
Watanabe et al. Clin Chem. 32/8, 1551-1544 (1986).
Chinese Office Action dated Oct. 10, 2020 in Application No. 2016800252936, entitled: Compositions and Methods for Allergen Detection.

* cited by examiner

COMPOSITIONS AND METHODS FOR ALLERGEN DETECTION

CROSS REFERENCE TO RELATED APPLICATIONS

This application is a Continuation application of U.S. patent application Ser. No. 15/569,808 filed Oct. 27, 2017, which is the 35 U.S.C. § 371 U.S. National Stage Entry of International Application No. PCT/US2016/029356 filed on Apr. 26, 2016, which claims priority to U.S. Provisional application No. 62/154,200 filed on Apr. 29, 2015, the contents of which are each incorporated herein by reference in their entirety.

REFERENCE TO THE SEQUENCE LISTING

The present application is being filed along with a Sequence Listing in electronic format. The Sequence Listing is provided as a file entitled 2066_1002USCON_SEQL-ST.txt, created on Sep. 18, 2019, which is 10,620 bytes in size. The information in the electronic format of the sequence listing is incorporated herein by reference in its entirety.

FIELD OF THE INVENTION

The present invention relates to aptamer based signaling polynucleotides (SPNs), compositions comprising such SPNs, assays and methods of using such SPNs for detection of a protein target, in particular a food allergen.

BACKGROUND OF THE INVENTION

Allergy is a serious medical condition affecting millions of people worldwide, with about 15 million people in the United States, including many children. During an allergic reaction, the immune system mistakenly targets an allergen as a threat and attacks it. The allergic reaction may affect the skin, the digestive system, the gastrointestinal tract, the respiratory system, the circulatory system and the cardiovascular system; and in some allergic reactions, multiple organ systems are affected. Allergic reactions range from mild to severe or life-threatening. Severe symptoms may include difficulty in breathing, low blood pressure, chest pain, loss of consciousness, and anaphylaxis. Food allergies are a major health issue in all industrialized countries. People having food allergies currently manage their allergies by avoiding any food that might contain that specific allergen. These restrictions have a major impact on the patients' quality of life and there remains no method for assessing the true allergen content of food. In the United States, food allergy symptoms send someone to the emergency room every three minutes.

Allergen detection is important for many reasons. A fast and accurate detection method and a portable device that can be easily operated by a person with food allergies to test their food and determine accurately and immediately the allergen content will be beneficial to provide for an informed decision on whether to consume or not. In food industry, allergen detection is critical to ensure accuracy of food labeling and to clean contaminants effectively during food production.

Currently available methods for detecting allergens mostly use antibodies based immunochemical methods (e.g., ELISA, lateral flow devices), peptides (e.g., mass spectrometry), enzymes, DNA based methods (e.g., PCR) and other generic/non-specific methods (e.g., visual inspection, ATP tests). These methodologies sometime are very complex, expensive, time consuming and unreliable. A fast and accurate method for determining the absence/presence of an allergen would be of great benefit. Ultrasensitive detection molecules that can detect a trace of an allergen(s) would be essential for developing a sensitive detection method.

Aptamers, which are single stranded (ss) DNA and RNA molecules, can bind to their targets due to their specific three dimensional structures; they offer specific properties which favor them as new detection molecules for protein recognition including allergens. Aptamers and aptamer-based assays have been shown, among many other useful applications (e.g., diagnostic tests) as a promising alternative in food safety control. A recent review describes analytical strategies developed using aptamers for the control of pathogens, allergens, adulterants, toxins and other forbidden contaminants to ensure food safety (Amaya-Gonzalez, et al., *Aptamer-Based Analysis: A Promising Alternative for Food Safety Control*, Sensors, 2013, 13:16292-16311; and Amaya-Gonzalez, et al., *Aptamer binding to coelic disease-triggering hydrophobic proteins: Towards a sensitive gluten detection system*. Anal. Chem. 2014, 86(5), 2733-2739). A method of detection of gluten is also described in PCT Publication PCT/ES2013/000133, 28 Jun. 2013, to Amaya-Gonzalez, et al. Other examples include PCT application publication NOs.: WO2013064818 and WO2012081908 (aptamers that specifically bind *Staphylococcus aureus*); WO2012081906 (aptamers for ompc protein in *Salmonella tiphimirium* strain); WO2009070749 (aptamers for detecting *salmonella* contamination); and U.S. Pat. Nos. 7,645,582 and 7,838,242 (aptamers that bind to *listeria* surface proteins) (each of which is incorporated herein by reference in its entirety.)

The present invention provides new aptamer based signaling polynucleotides, compositions comprising such SPNs, and fast, sensitive and accurate assays to detect the absence or presence of allergens, and/or to quantitatively measure the amount of allergen in test samples. The signaling polynucleotides and detection assays developed in the present disclosure may be used in any allergen detection devices in the art, such as microfluidic chips taught in U.S. Pat. No. 8,617,903 and portable devices taught in the commonly owned PCT patent application NO.: PCT/US14/62656 filed on Oct. 28, 2014, and U.S. provisional application No. 62/133,632 filed on Mar. 16, 2015 (each of which is incorporated herein by reference in its entirety).

SUMMARY OF THE INVENTION

The present invention relates to compositions, compounds, assays and methods for detecting one or more allergens in a sample. In some embodiments, allergens are food allergens.

In some embodiments, compositions of the present invention comprise nucleic acid aptamer based signaling polynucleotides (SPNs) that can specifically bind to an allergen with high affinity. In other embodiments, said SPN further comprises a fluorophore at one end of the nucleic acid sequence and a quencher at the opposite end. The SPNs of the present invention may comprise a polynucleotide sequence wherein 5 to 20 nucleobase residues at the 5'-end of the sequence are at least 80% complementary to 5 to 20 nucleobase residues at the 3"-end of the sequence capable of forming a hairpin structure, thereby bringing the quencher in sufficient proximity to the fluorophore for quenching the fluorescence of the fluorophore.

In some embodiments, a SPN may comprise a polynucleotide sequence selected from the sequences listed in Table 1 of the present disclosure.

In some embodiments, provided in the present invention are assays and methods for detection of one or more allergens in a test sample. In some embodiments, the methods may comprise the steps of (a) obtaining a test sample suspected of containing an allergen; (b) processing the test sample and extracting proteins from the processed sample using an extraction buffer; (c) mixing the protein extraction of step (b) with a SPN that specifically binds to the allergen; (d) activating the SPN by means of an energy excitation; and (e) visualizing the interaction between the SPN and the allergen protein and detecting the absence or presence of the allergen in the test sample. In some embodiments, total proteins extracted from the test sample are determined and the extraction buffer is optimized for maximal protein extraction. In other embodiments, the amount of the allergen presented in the test sample is determined.

DETAILED DESCRIPTION OF THE INVENTION

Figure 1:
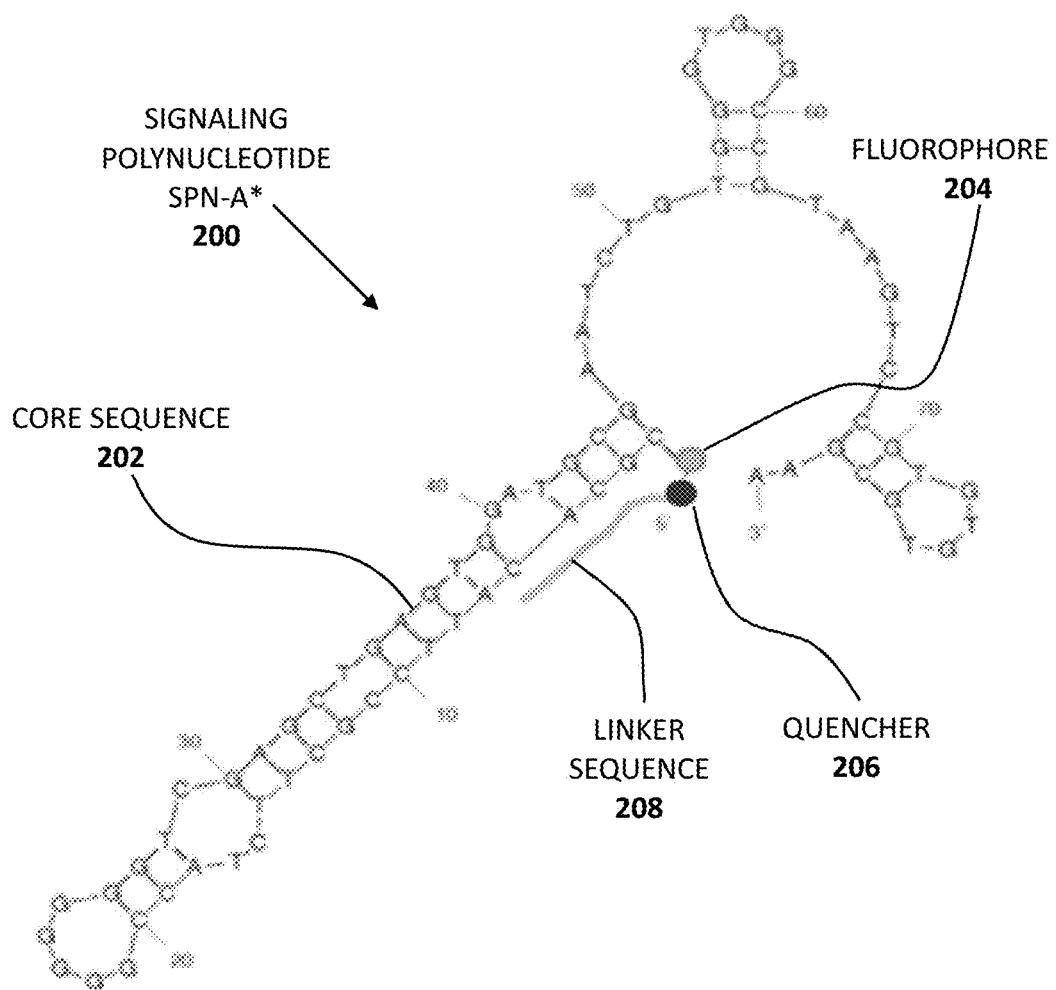
FIG. 1 shows the secondary sequence of a detection molecule represented by signaling polynucleotide SPN-A* 200 (SEQ ID NO.: 2) which comprises core sequence 202 (SEQ ID NO.: 1), fluorophore 204, quencher 206 and linker sequence 208 (SEQ ID NO.: 3).

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

Nucleic acid aptamers that can specifically bind to an allergen protein with high affinity are selected and signaling polynucleotides are designed using selected aptamers and tested for detection of an allergen in the present disclosure.

Allergens include those from food products, the environment or animals such as a domestic pet dander. Food allergens include, but are not limited to proteins in legumes such as peanuts, peas, lentils and beans, tree nuts, wheat, milk, fish, egg white and sea food. Other allergens may be from the environment such as pollens, other animals (e.g., pet), pathogens and medicines. A comprehensive list of allergenic proteins from various sources is discussed below.

Composition of the Invention

Described herein are compositions, methods for the design, preparation, use and manufacture of the compositions, and methods and assays for detection of a target protein(s) in a sample, in particular an allergen protein(s).

Aptamers

In accordance with the present invention, compositions of the present invention include, but are not limited to any molecule or molecules which are capable of association or binding to one or more allergens. In some embodiments, compositions of the invention comprise one or more aptamers.

As used herein, an "aptamer" is a nucleic acid species that has been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Nucleic acid aptamers have specific binding affinity to molecules through interactions other than classic Watson-Crick base pairing. Nucleic acid aptamers, like peptides generated by phage display or monoclonal antibodies (mAbs), are capable of specifically binding to selected targets and, through binding, block their targets' ability to function. In some cases, aptamers may also be peptide aptamers. As used herein, an "aptamer" specifically refers to a nucleic acid aptamer.

Aptamers, often called "chemical antibodies," have characteristics which are similar to those of antibodies. A typical nucleic acid aptamer is approximately 10-15 kDa in size (20-45 nucleotides), binds its target with at least nanomolar affinity, and discriminates against closely related targets.

Nucleic acid aptamers may be either monovalent or multivalent. Aptamers may be monomeric, dimeric, trimeric, tetrameric or higher multimeric. Individual aptamer monomers may be linked to form multimeric aptamer fusion molecules. As a non-limiting example, a linking oligonucleotide (i.e., linker) may be designed to contain sequences complementary to both 5'-arm and 3'-arm regions of random aptamers to form dimeric aptamers. For trimeric or tetrameric aptamers, a small trimeric or tetrameric (i.e., a Holiday junction-like) DNA nanostructure will be engineered to include sequences complementary to the 3'-arm region of the random aptamers, therefore creating multimeric aptamer fusion through hybridization. In addition, 3 to 5 or 5 to 10 dT rich nucleotides can be engineered into the linker polynucleotides as a single stranded region between the aptamer-binding motifs, which offers flexibility and freedom of multiple aptamers to coordinate and synergize multivalent interactions with cellular ligands or receptors.

Alternatively, multimeric aptamers can also be formed by mixing biotinylated aptamers with streptavidin.

As used herein, the term "multimeric aptamer" or "multivalent aptamer" refers to an aptamer that comprises multiple monomeric units, wherein each of the monomeric units can be an aptamer on its own. Multivalent aptamers have multivalent binding characteristics. A multimeric aptamer can be a homomultimer or a heteromultimer. The term "homomultimer" refers to a multimeric aptamer that comprises multiple binding units of the same kind, i.e., each unit binds to the same binding site of the same target molecule. The term "heteromultimer" refers to a multimeric aptamer that comprises multiple binding units of different kinds, i.e., each binding unit binds to a different binding site of the same target molecule, or each binding unit binds to a binding site on different target molecule. Thus, a heteromultimer can refer to a multimeric aptamer that binds to one target molecule at different binding sties or a multimeric aptamer that binds to different target molecules. A heteromultimer that binds to different target molecules can also be referred to as a multi-specific multimer.

Nucleic acid aptamers comprise a series of linked nucleosides or nucleotides. The term "nucleic acid," in its broadest sense, includes any compound and/or substance that comprise a polymer of nucleotides. These polymers are often referred to as polynucleotides. Exemplary nucleic acid molecules or polynucleotides of the invention include, but are not limited to, either D- or L-nucleic acids, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure, the ribofuranosyl ring or in the ribose-phosphate backbone.

Nucleic acid aptamers may be ribonucleic acid, deoxyribonucleic acid, or mixed ribonucleic acid and deoxyribonucleic acid. Aptamers may be single stranded ribonucleic acid, deoxyribonucleic acid or mixed ribonucleic acid and deoxyribonucleic acid.

In some embodiments, the aptamer comprises at least one chemical modification. In some embodiments, the chemical modification is selected from a chemical substitution of the nucleic acid at a sugar position, a chemical substitution at a phosphate position and a chemical substitution at a base position. In other embodiments, the chemical modification is selected from incorporation of a modified nucleotide; 3' capping; conjugation to a high molecular weight, non-immunogenic compound; conjugation to a lipophilic compound; and incorporation of phosphorothioate into the phosphate backbone. In a preferred embodiment, the high molecular weight, non-immunogenic compound is polyalkylene glycol, and more preferably is polyethylene glycol (PEG). The process of covalent conjugation of PEG to another molecule, normally a drug or therapeutic protein is known as PEGylation. PEGylation is routinely achieved by incubation of a reactive derivative of PEG with the target molecule. The covalent attachment of PEG to a drug or therapeutic protein can mask the agent from the host's immune system, thereby providing reduced immunogenicity and antigenicity, and increase the hydrodynamic size (size in solution) of the agent which prolongs its circulatory time by reducing renal clearance. PEGylation can also provide water solubility to hydrophobic drugs and proteins.

In another preferred embodiment, the 3' cap is an inverted deoxythymidine cap.

In some embodiments, nucleic acid aptamers are provided in which the P(O)O group is replaced by P(O)S ("thioate"), P(S)S ("dithioate"), P(O)NR2 ("amidate"), P(O)R, P(O)OR', CO or CH2 ("formacetal") or 3'-amine (—NH—CH2-CH2-), wherein each R or R' is independently H or substituted or unsubstituted alkyl. Linkage groups can be attached to adjacent nucleotide through an —O—, —N—, or —S— linkage. Not all linkages in the nucleic acid aptamers are required to be identical.

As non-limiting examples, a nucleic acid aptamer can include D-ribose or L-ribose nucleic acid residues and can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, an inverted deoxynucleoside or inverted ribonucleoside, a 2'-deoxy-2'-fluoro-modified nucleoside, a 2'-amino-modified nucleoside, a 2'-alkyl-modified nucleoside, a morpholino nucleoside, a phosphoramidate or a non-natural base comprising nucleoside, or any combination thereof. Alternatively, a nucleic acid aptamer can comprise at least two modified ribonucleosides, at least 3, at least 4, at least 5, at least 6, at least 7, at least 8, at least 9, at least 10, at least 15, at least 20 or more modified ribonucleosides, up to the entire length of the molecule. The modifications need not be the same for each of such a plurality of modified deoxy- or ribonucleosides in a nucleic acid molecule.

Detection molecules which are nucleic acid based may include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, those disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993.

A suitable nucleotide length for an aptamer ranges from about 15 to about 100 nucleotides (nt), and in various other preferred embodiments, 15-30 nt, 20-25 nt, 30-100 nt, 30-60 nt, 25-70 nt, 25-60 nt, 40-60 nt, 25-40 nt, 30-40 nt, any of 18, 19, 20, 21, 22, 23, 24, 25, 26, 27, 28, 29, 30, 31, 32, 33, 34, 35, 36, 37, 38, 39 or 40 nt or 40-70 nt in length. In some embodiments, an aptamer may be 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 nt in length. In other embodiments, an aptamer may be 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nt in length. However, the sequence can be designed with sufficient flexibility such that it can accommodate interactions of aptamers with two targets at the distances described herein.

In some embodiments, the nucleic acid aptamer comprises one or more regions of double-stranded character. Such double stranded regions may arise from internal self-complementarity or complementarity with a second or further aptamers or oligonucleotide molecule. In some embodiments, the double stranded region may be from 4-12, 4-10, 4-8 base pairs in length. In some embodiments, the double stranded region may be 5, 6, 7, 8, 9, 10, 11 or 12 base pairs. In some embodiments, the double stranded region may form a stem region. Such extended stem regions having double stranded character can serve to stabilize the nucleic acid aptamer. As used herein, the term "double stranded character" means that over any length of two nucleic acid molecules, their sequences form base pairings (standard or nonstandard) of more than 50 percent of the length.

Aptamers may be further modified to provide protection from nuclease and other enzymatic activities. The aptamer sequence can be modified by any suitable methods known in the art. For example, phosphorothioate can be incorporated into the backbone, and 5'-modified pyrimidine can be included in 5' end of ssDNA for DNA aptamers. For RNA aptamers, modified nucleotides such as substitutions of the 2'—OH groups of the ribose backbone, e.g., with 2'-deoxy-NTP or 2'-fluoro-NTP, can be incorporated into the RNA molecule using T7 RNA polymerase mutants. The resistance of these modified aptamers to nuclease can be tested by incubating them with either purified nucleases or nuclease from mouse serum, and the integrity of aptamers can be analyzed by gel electrophoresis.

In some embodiments, such modified nucleic acid aptamers may be synthesized entirely of modified nucleotides, or with a subset of modified nucleotides. The modifications can be the same or different. All nucleotides may be modified, and all may contain the same modification. All nucleotides may be modified, but contain different modifications, e.g., all nucleotides containing the same base may have one type of modification, while nucleotides containing other bases may have different types of modifications. For example, all purine nucleotides may have one type of modification (or are unmodified), while all pyrimidine nucleotides have another, different type of modification (or are unmodified). In this way, oligonucleotides, or libraries of oligonucleotides are generated using any combination of modifications as disclosed herein.

According to certain embodiments of the present invention, variants and derivatives of aptamers are provided. The term "derivative" is used synonymously with the term "variant" and refers to a molecule that has been modified or changed in any way relative to a reference or starting aptamer. The nucleic acid sequence of aptamer variants may possess substitutions, deletions, and/or insertions at certain positions within the nucleotide sequence, as compared to a reference or starting sequence. Ordinarily, variants will possess at least about 50% identity (homology) to a reference sequence, and preferably, they will be at least about 80%, more preferably at least about 90% identical (homologous) to a reference sequence.

In some embodiments, variant mimics of aptamers of the present invention are provided. As used herein, the term "variant mimic" is one which contains one or more nucleic acids which would mimic an activated sequence. The nucleic acid sequences of variant mimics may comprise naturally occurring nucleic acids, or alternatively, non-naturally occurring nucleic acids.

Aptamer Conjugates and Labels

In some embodiments, aptamers of the invention may comprise conjugates. Such conjugates of the invention may include a naturally occurring substance or ligand, such as a protein; a carbohydrate (e.g., a dextran, pullulan, chitin, chitosan, inulin, cyclodextrin or hyaluronic acid); or a lipid; as well as a recombinant or synthetic molecule, such as a synthetic polymer.

Examples of conjugates may include, but are not limited to magnetic nanoparticles (MNPs) (e.g., superparamagnetic Iron Oxide Nanoparticles (SPIONs), gold NPs, and quantum dots (QDs)); chitosans; and drug conjugates.

In some embodiments, aptamers of the present invention may comprise a detectable agent, such as various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., 18F, 67Ga, 81mKr, 82Rb, 111In, 123I, 133Xe, 201Tl, 125I, 35S, 14C, 3H, or 99mTc (e.g., as pertechnetate (technetate(VII), TcO4)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2'-disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), dichlorotriazin-2-yl)aminofluorescein (DTAF), 2',7'-dimethoxy-4',5'-dichloro-6-carboxyfluorescein, fluorescein, fluorescein isothiocyanate, X-rhodamine-5-(and-6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with N,N-diethylethanamine (1:1) (IR144); 5-chloro-2-[2-[3-[(5-chloro-3-ethyl-2(3H)-benzothiazol-ylidene)ethylidene]-2-(diphenylamino)-1-cyclopenten-1-yl]ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives (e.g., pyrene, pyrene butyrate, and succinimidyl 1-pyrene); butyrate quantum dots; Reactive Red 4 (CIBA-CRON™ Brilliant Red 3B-A); rhodamine and derivatives (e.g., 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable agent may be a non-detectable pre-cursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))). In some embodiments, the non-detectable precursor comprises a combination of a fluorophore and a quencher, such as the combination of fluorescein and DABCYL, for example. Guidelines for selection of fluorophore and quencher pairs are described in S. A. E. Marras *Selection of Fluorophore and Quencher Pairs for Fluorescent Nucleic Acid Hybridization Probes* in Didenko, Vladimir V., ed. *Fluorescent energy transfer nucleic acid probes: designs and protocols*. Vol. 335. Springer, 2006, which is incorporated herein by reference in entirety.

Signaling Polynucleotides (SPNs)

In accordance with certain embodiments, there are provided polynucleotide sequences that are detectable when bound at high affinity and specificity to allergen targets. Such polynucleotide sequences may be produced using the SELEX process as described hereinabove.

In certain types of exemplary signaling polynucleotides, the 5' end of the sequence is bound to a fluorescent molecule and the 3' end carries a 5-20 nucleotide long reverse-complement sequence that binds to the 5'-end. This results of folding of the sequence and formation of a stem-loop structure. A quencher molecule is bound to the 3'-end. The skilled person will recognize that alternative arrangements are possible wherein the quencher is bound to the 5'-end and the fluorophore is bound to the 3'-end. Such alternative signaling polynucleotides may be prepared by the skilled person in context of the present description without undue experimentation.

An exemplary signaling polynucleotide designed with a stem-loop structure for binding to lysozyme as a molecular target will be described herein below in Example 1.

In certain embodiments, the fluorophore molecule at the 5'-end is bound to a T nucleotide residue in order to prevent quenching caused by a G nucleotide residue.

In recognition that higher melting temperatures (Tm) are to be avoided, the Tm or AG of the two strands will need to be lower than the binding affinity of the molecular target in order for the signaling polynucleotide to have a thermodynamic preference for binding to the molecular target. In order to retain preferable molecular target binding, $Mg^{+2}$ or $K^+$ may be added to shift the equilibrium. Addition of up to about 37 mM KCl will shift the equilibrium of a given signaling polynucleotide to favor binding of a molecular target while adding up to about 5 mM $MgCl_2$ will shift the equilibrium towards retention of the double strand structure, thereby lowering the affinity of the signaling polynucleotide for its molecular target.

It is not necessary for the two reverse complementary strands to be on opposite sides in order to create a stem-loop structure. The reverse complementary strand can be attached/annealed to the 5'-end. The sequence must be long enough to physically interfere with the structure. The double strand binding needs to prevent the formation of the secondary structure folding which is needed in order to bind the molecular target.

In certain embodiments, the signaling polynucleotides are dimeric entities with a core sequence linked to a fluorophore and a shorter annealed linker sequence linked to a quencher, or vice versa. In one example, the signaling polynucleotide may comprise a linker sequence 5 to 20 nucleobases in length annealed to the 5'-end of the sequence of the signaling polynucleotide and having at least 80% complementarity with the 5'-end of the sequence of the signaling polynucleotide, wherein the signaling polynucleotide comprises a fluorophore and the linker sequence comprises a quencher.

In certain embodiments, the signaling polynucleotide sequences are chemically modified with 2"-O-methyl modifications. Such modifications are expected to not significantly affect the binding affinity and sensitivity with respect to binding of the molecular target, while enhancing stability.

In some embodiments, signaling polynucleotides against several common food allergens are designed using polynucleotides (e.g., aptamers) selected from SELEX processes as described above herein. The nucleic acid sequences of such aptamers have high binding affinity and specificity to the allergens. Table 1 lists the aptamer sequences from which the signaling polynucleotides are designed.

TABLE 1

SPNs that bind to food allergens

| Allergen | Reference No. | Sequence (5'-3') | SEQ ID NO. |
|---|---|---|---|
| Peanut | MB4 | {FAM}TTCGCGCACATTCCGCTTCTACCGGGGGGG TCGAGCTGAGTGGATGCGAATCTGTGGGTGGGCC GTAAGTCCGTGTGTGCGAA{DABCYL} | 8 |
| Peanut | MB7 | {FAM}TCGCACATTCCGCTTCTACCGGGGGGTCG AGCTGAGTGGATGCGAATCTGTGGGTGGGCCGTA AGTCCGTGTGTGCGAAAATGTGCGA{DABCYL} | 9 |
| Peanut | MB9 | {FAM}TCGCACATTCCGCTTCTACCGGGGGGGTCG AGCTGAGTGGATGCGAATCTGTGGGTGGGCCGTA AGTCCGTGTGTGCGAATGTGCGA{DABCYL} | 10 |
| Egg white | E-MB7 | {FAM}TGGCAGCTAAGCAGGCGGCTCACAAAACC ATTCGCATGCGGCTGTTCCA{DABCYL} | 11 |

TABLE 1-continued

SPNs that bind to food allergens

| Allergen | Reference No. | Sequence (5'-3') | SEQ ID NO. |
|---|---|---|---|
| Egg white | E-MB6 | {FAM}TGCAGCTAAGCAGGCGGCTCACAAAACCA TTCGCATGCGGCGCTGCA{DABCYL} | 12 |
| Egg white | E-MB4 | {FAM}TGCAGCTAAGCAGGCGGCTCACAAAACCA TTCGCATGCGGCTGCA{DABCYL} | 13 |
| Egg white | E-MB5 | {FAM}GCAGCTAAGCAGGCGGCTCACAAAACCAT TCGCATGCGGCGCTGC{DABCYL} | 14 |
| Wheat | Gli4 + 4 | {FAM}TTTCCCAGTCTCCCGTTTACCGCGCCTACA CATGTCTGAATGCCGAAA{DABCYL} | 15 |
| Wheat | GL1_7_4 | {FAM}TCGAAAAGCTGCAGCTGCAACCATTTCCGC AGCCGCAACTACCATATCCGCAGCCGCAACTACC ATATCCGCAGCCGCAACTACCATATCCGCAGCGG CAACCATTTTCGA{DABCYL} | 16 |
| Wheat | G33_16_1/2 | {FAM}AACAAACTACTAACTAGGTAAGATCACGC AGCACTAAACGACGTAGTTGCCATGTT{DABCYL} | 17 |
| Wheat | G33_7 | {FAM}TGGCAAACTACTAACTAGGTAAGATCACG CAGCACTAAACGACGTAGTTGCCA{DABCYL} | 18 |
| Wheat | G33_14_1/2 | {FAM}TTGGAAACTACTAACTAGGTAAGATCACG CAGCACTAAACGACGTAGTTGCCAA{DABCYL} | 19 |
| Wheat | S_Gluten_ 11_7_1/2 | {FAM}CCGAGCTAAATGCTGCAGCTGCAACCATTT CCGCAGCCGCAACTACCATATCCGCAGCCGCAAC TACCATATCCGCAGCCGCAACTACCATATCCGCA GCGGCAACCATTTAGCTCGG{DABCYL} | 20 |
| Wheat | S_Gluten_ 8_4_1 | {FAM}CCGAAAATGCTGCAGCTGCAACCATTTCCG CAGCCGCAACTACCATATCCGCAGCCGCAACTAC CATATCCGCAGCCGCAACTACCATATCCGCAGCG GCAACCATTTTCGG{DABCYL} | 21 |
| Wheat | GLI_6 1/2/3 | {FAM}CCAGTCTCCCGTTTACCGCGCCTACACATG TCTGAATGCCGACTGG{DABCYL} | 22 |
| Wheat | GLI_4 1/2 | {FAM}GGCACCAGTCTCCCGTTTACCGCGCCTACA CATGTCTGAATGCC{DABCYL} | 23 |
| Milk | 457_12 | {FAM}AUGAGCUUGGUCACCUUUCCUGACAUUA ACACAGGCGAAACGGUGAAAGCCGU{DABCYL} | 24 |
| Milk | 491_5E/F | {FAM}CAUGAGUUUUCCCGAUACGGCUACGAAU UGCGACAACGAAACGGUGAAAGCCGUG{DABCYL} | 25 |
| Milk | 491_2_11 | {FAM}UGAGUUUUCCCGAUACGGCUACGAAUUG CGACAACGAAACGGUGAAAGCCCA{DABCYL} | 26 |

In addition to the nucleic acid aptamers selected from the SELEX process as described in Examples. Signaling polynucleotides may be designed using aptamers selected from other studies. The 5'-end and 3' end nucleotides, fluorophores/quencher pairs and the stem-loop structures may be further designed according to the criteria described above, and tested for their binding affinity and specificity to the target.

In some embodiments, SPNs may be developed using aptamers against food allergens as disclosed in the art. Such aptamers may include, but are not limited to, aptamers specific to Lup an 1 (β-conglutin) (Nadal P et al., *DNA Aptamers against the Lup an 1 Food Allergen*, PLos One, 2012, 7: e35253); leptin (lep3) (Ashley and Li, *Three-dimensional selection of leptin aptamers using capillary electrophoresis and implications for clone validation*, Anal Biochem., 2013, 434: 146-152); and lysozyme (egg white) (Kirby et al., *Aptamer-based sensor arrays for the detection and quantitation of proteins*, Anal Chem. 2004, 76(14): 4066-4075; Zou M et al., *The homogeneous fluorescence anisotropic sensing of salivary lysozyme using the 6-carboxyfluorescein-labeled DNA aptamer*, Biosens Bioelectron, 2012, 32(1): 148-154; Robertson and Ellington, *In vitro selection of nucleootein enzymes*, Nature Biotechnology, 2001: 650-655; and Hesselberth et al, *Simultaneous detection of diverse analytes with an aptazyme ligase array*, Analytical Biochemistry, 2003, 312: 106-112; each of which is incorporated herein by reference in its entirety.) The nucleic acid sequences of the aptamers from each disclosure are listed in Table 2.

In some embodiments, signaling polynucleotides may be developed using aptamers that bind to Cry j 2 allergen of Japanese cedar pollen (Ogihara et al., *DNA aptamers against Cry j 2 allergen of Japanese cedar pollen for biosensing* applications, Biosens Bioelectron., 2015, 63, 159-165), lup an 1 (β-conglutin) subunit present in lupine flour (Svobodova et al., *Ultrasensitive aptamer based detection of β-conglutin food allergen*, Food Chem., 2014, 165, 419-423; and Mairal et al., *FRET-based dimeric aptamer probe for selective and sensitive Lup an 1 allergen detection*, Biosens Bioelectron., 2014, 54: 207-210), and gliadin (gluten) (Pinto A et al., *Label-free detection of gliadin food allergen mediated by real-time apta-PCR*, Anal Bioanal Chem., 2014, 406(2): 515-524); each of which is incorporated herein by reference in its entirety.

2013, 23: 878-884; Hyeon, J. et al. *Development of RNA Aptamers for Detection of Salmonellas Enteritidis*, Journal of Microbiological Methods, 2012, 89:79-82; Ohk et al., *Antibody-aptamer functionalized fibre-optic biosensor for specific detection of Listeria monocytogenes from food*, J. Appl. Microbiol., 2010, 109: 808-817; Li, H. et al., Aptamer selection for the detection of *Escherichia coli* K88, Canadian Journal of Microbiology, 2011, 57: 453-459; Lee at al., *In vitro selection of Escherichia coli O157:H7-specific RNA aptamer*, Biochemical and Biophysical Research Commu-

TABLE 2

Aptamers against food allergens

| Allergen | Reference | Sequence (5'-3') | SEQ ID NO. |
|---|---|---|---|
| Lup an 1 | Nadal et al., Plos One, 2012, 7: e35253 | AGCTGACACAGCAGGTTGGTGGGGTGGCTTCC AGTTGGGTTGACAATACGTAGGGACACGAAGT CCAACCACGAGTCGAGCAATCTdCGApAAT | 27 |
| Lup an 1 | Nadal et al., Anal. Bioanal. Chem., 2013, 405: 9343-9349 | GGTGGGGGTGG | 28 |
| Lep 3 (leptin) | Ashley and Li, Anal Biochem., 2013, 434: 146-152 | CTTCTGCCCGCCTCCTTCCGTTAATGGGGGATCT CGCGGCCGTTCTTGTTGCTTATACAGGAGACGA GATAGGCGGACACT | 29 |
| Lysozyme (Egg white) | Kirby et al., Anal Chem. 2004, 76(14): 4066-4075 | GGGAATGGATCCACATCTACGAATTCATCAGGG CTAAAGAGTGCAGAGTTACTTAGTTCACTGCAG ACTTGACGAAGCTT | 30 |
| Lysozyme (Egg white) | Zou M et al., Biosens Bioelectron, 2012, 32(1): 148-154 | AGCAGCACAGAGGTCAGATGGCAGGTAAGCAG GCGGCTCACAAAACCATTpdCGCATGCGGCCCT ATGCGTGCTACCGTGAA | 31 |
| Lysozyme (Egg white) | Robertson and Ellington, 2001, Nature Biotech., 2001, 650-655 | rGGAprCCUprCGGprCGAprAAGprCprUAAprCGUpr CUCprAUGprGCUprAAAprUUGprCCAprUGUprUG CprUACprAAAprUGAprUAUprGACprUAGprAprGA GprGUUprAGGprUGCprCUCprGUGprAUGprUCCpr AGUprCGCp | 32 |

In some embodiments, signaling polynucleotides may be developed using aptamers that are selected as detection molecules for pathogens. As non-limiting examples, aptamers that can specifically recognize *Salmonella, Listeria, E. coli*, and *Aspergillus fumigatus* may be used to design signaling polynucleotides (SPNs) as described herein. Such aptamers are discussed in, for example: Han and Lee, *In Vitro Selection of RNA Aptamer Specific to Salmonella Typhimurium*, Journal of Microbiology and Biotechnology, nications, 2012, 417: 214-220; Ali et al., *Fluorogenic DNAzyme obes as Bacterial Indicators*, Angewandte Chemie International Edition, 2011, 50: 3751-3754; and DeGrasse J A, *A Single-Stranded DNA Aptamer That Selectively Binds to Staphylococcus aureus Enterotoxin B*, Plos One, 2012, 7: e33410; each of which is incorporated herein by reference in its entirety. Table 3 lists the sequences of such aptamers from those disclosures.

TABLE 3

Aptamers against pathogens

| Pathogen | Reference | Sequence (5'-3') | SEQ ID NO. |
|---|---|---|---|
| *Salmonella* | Han and Lee, J. Microbio. & Biotech., 2013, 878-884 | fUAGfUGfUGAGAGfCCGfUGAGfUGAAAGGf CfCGfCGAfCAAAGAfUfCGGA ((f = 2'-f-pyrimidines) | 33 |

TABLE 3-continued

Aptamers against pathogens

| Pathogen | Reference | Sequence (5'-3') | SEQ ID NO. |
|---|---|---|---|
| Salmonella Enteritidis | Hyeon, J. et al., J. Microbio. Methods, 2012, 79-82 | GGGUUCACUGCAGACUUGACGAAGCUUG AGAGAUGCCCCCUGAUGpUGCAUUCUUG UUGUGUUGCGGCAAUGGAUCCACAUCUA CGAAUUC | 34 |
| Listeria | Ohk et al., J. Appl. Microbiol., 2010, 109: 808-817 | ATCCATGGGCGGAGATGAGGGGGAG GAGGGCGGGTACCCGGTTGAT | 35 |
| E. coli fimbriae otein K88 | Li et al., Canadian Journal of Microbiology, 2011, 57: 453-459. | GGAGACCGTACCATCTGTTCGTGGAAGCG CTTTGCTCGTCCATTAGCCTTGTGCTCGTG C | 36 |
| E. coli O157:H7 | Lee et al., Biophysical Research Communications, 2012, 417: 214-220 | GGGfUfCfUfUfCfCfUGGAfCfUGfUfCGAAAA fUfUfCAGfUAfUfCGGGAGGfUfUAfCGfUAfU fUfUGGfUfUfUAfUAGAfUAGfUAA (f = 2'-f-pyrimidines) | 37 |
| E. Coli mixture | Ali et al., Angewandte Chemie International Edition, 2011, 50: 3751-3754 | CACGGATCCTGACAAGGATGTGTGCGTTG TCGAGACCTGCGACCGGAACACTACACTG TGTGGGATGGATTTCTTTACAGTTGTGTGC AGCTCCGTCCGACT CTTCCTAGC-{Internal/Fluorescein-dT}-Aptamer-{Internal/Dabcyl-dT}-GGTTCGATCAAGA | 38 |
| Staphylococcus aureus (enterotoxin B) | DeGrasse JA, Plos One, 2012, 7: e33410 | GGTATTGAGGGTCGCATCCACTGGTCG TTGTTGTCTGTTGTCTGTTATGTTGTTTCG TGATGGCTCTAACTCTCCTCT | 39 |

In other embodiments, as a skilled artisan would envision, aptamers that specifically bind to non-protein targets, for example, a small molecule may also be used to design signaling polynucleotides as disclosed herein. Table 4 lists the sequences of some aptamers as non-limiting examples (Ferguson et al., *A novel strategy for selection of allosteric ribozymes yields RiboReporter™ sensors for caffeine and aspartame*, Nucleic Acids Research, 2004, 32: 1756-1766; and Ono and Togashi, *Highly selective oligonucleotide-based sensor for mercury(II) in aqueous solutions*, Angew. Chem. Int. Ed., 2004, 43: 4300-4302).

Targets of the Signaling Polynucleotides

The present invention provides aptamer based signaling polynucleotides (SPNs) that bind to a target molecule. As stated below, the target molecule may be an allergen protein or variants thereof. In some embodiments, SPNs may be designed to bind or associate with proteins or other biomolecules which themselves associated with the allergen.

According to the present invention, and while not wishing to be bound by theory, the detection polynucleotides may completely or partially bind an allergen.

TABLE 4

Aptamers against non-protein targets

| Non protein target | Reference | Sequence (5'-3') | SEQ ID NO. |
|---|---|---|---|
| Caffeine | Ferguson et al., Nucleic Acids Research, 2004, 32: 1756-1766 | GGAUGUCCAGUCGCUUGCAAUGCCCUUU UAGACCCUGAUGAGGAUCAUCGGACUUU GUCCUGUGGAGUAAGAUCGCGAAACGGU GAAAGCCGUAGGUCU | 40 |
| Mercury II (Hg2+) | Ono and Togashi, Angew. Chem. Int. Ed., 2004,43:4300-4302 | TTCTTTCTTCCCCTTGTTTGTT | 41 |

Allergens

In some embodiments, allergens are food allergens. Examples of allergenic proteins associated with food include, but are not limited to, Brine shrimp (Art fr 5), Crab (Cha f 1), North Sea Shrimp (Cra c 1, Cra c 2, Cra c 4, Cra c 5, Cra c 6, Cra c 8), American lobster (Hom a 1, Hom a 3, Hom a 6), white shrimp (Lit v 1, Lit v 2, Lit v 3, Lit v4), giant freshwater prawn (Mac r 1), shrimp (Met e 1, Pen a 1, Pen i 1), northern shrimp (Pan b 1), spiny lobster (Pan s 1), black tiger shrimp (Pen m 1, Pen m 2, Pen m 3, Pen m 4, Pen m 6), narrow-clawed crayfish (Pon i 4, Pon i 7), blue swimmer crab (Por p 1), domestic cattle (Bos d 4, Bos d 5, Bos d 6, Bos d 7, Bos d 8, Bos d 9, Bos d 10, Bos d 11, Bos d 12), Atlantic herring (Clu h 1), common carp (Cyp c 1), Baltic cod (Gad c 1), Atlantic cod (Gad m 1, Gad m 2, Gad m 3), cod (Gad c 1), chicken (Gal d 1, Gal d 2, Gal d 3, Gal d 4, Gal d 5), Barramunda (Lat c 1), Lepidorhombus whiffiagonis (Lep w 1), chum salmon (Onc k 5), Atlantic salmon (Sal s 1, Sal s 2, Sal s 3) rainbow trout (Onc m 1), Mozambique tilapia (Ore m 4), edible frog (Ran e 1, Ran e 2), pacific pilchard (Sar sa 1), ocean perch (Seb m 1), yellowfin tuna (Thu a 1, Thu a 2, Thu a 3), swordfish (Xip g 1), abalone (Hal m 1), brown garden snail (Hel as 1), Squid (Tod p 1), pineapple (Ana c 1, Ana c 2), asparagus (Aspa o 1), barley (Hor v 12, Hor v 15, Hor v 16, Hor v 17, Hor v 20, Hor v 21), banana (Mus a 1, Mus a 2, Mus a 3, Mus a 4, Mus a 5), banana (Musxpl), rice (Ory s 12), rye (Sec c 20), wheat (Tri a 12, Tri a 14, Tri a 18, Tri a 19, Tri a 25, Tri a 26, Tri a 36, Tri a 37), maize (corn) (Zea m 14, Zea m 25), kiwi fruit (Act cl, Act c 2, Act c 5, Act c 8, Act c 10, Act d 1, Act d 2, Act d 3, Act d 4, Act d 5, Act d 6, Act d 7, Act d 8, Act d 9, Act d 10, Act d 11), cashew (Ana o 1, Ana o 2, Ana o 3), celery (Api g 1, Api g 2, Api g 3, Api g 4, Api g 5, Api g 6), peanut (Ara h 1, Ara h 2, Ara h 3, Ara h 4, Ara h 5, Ara h 6, Ara h 7, Ara h 8, Ara h 9, Ara h 10, Ara h 11, Ara h 12, Ara h 13), brazil nut (Ber e 1, Ber e 2), oriental mustard (Bra j 1), rapeseed (Bra n 1), cabbage (Bra o 3), turnip (Bra r 1, Bra r 2), bell pepper (Cap a 1w, Cap a 2), pecan (Car i 1, Car i 4), chestnut (Cas s 1, Cas s 5, Cas s 8, Cas s 9), lemon (Cit l 3), tangerine (Cit r 3), sweet orange (Cit s 1, Cit s 2, Cit s 3), Hazel (Cor a 1, Cor a 2, Cor a 8, Cor a 9, Cor a 11, Cor a 12, Cor a 13, Cor a 14), muskmelon (Cuc m 1, Cuc m 2, Cuc m 3), carrot (Dau c 1, Dau c 4, Dau c 5), common buckwheat (Fag e 2, Fag e 3), tartarian buckwheat (Fag t 2), strawberry (Fra a 1, Fra a 3, Fra a 4), soybean (Gly m 1, Gly m 2, Gly m 3, Gly m 4, Gly m 5, Gly m 6, Gly m 7, Gly m 8), sunflower (Hel al, Hel a 2, Hel a 3), black walnut (Jug n 1, Jug n 2), English walnut (Jug r 1, Jug r 2, Jug r 3, Jug r 4), Cultivated lettuce (Lac s 1), Lentil (Len c 1, Len c 2, Len c 3), litchi (Lit c 1), narrow-leaved blue lupin (Lup an 1), apple (Mal d 1, Mal d 2, Mal d 3, Mal d 4), Cassava (Man e 5), mulberry (Mor n 3), avocado (Pers a 1), green bean (Pha v 3), pistachio (Pis v 1, Pis v 2, Pis v 3, Pis v 4, Pis v 5), pea (Pis s 1, Pis s 2), apricot (Pm ar 1, Pm ar 3), sweet cherry (Pm av 1, Pm av 2, Pm av 3, Pm av 4), European plum (Pm d 3), almond (Pm du 3, Pm du 4, Pm du 5, Pm du 6), peach (Pm p 1, Pm p 2, Pm p 3, Pm p 4, Pm p 7), pomegranate (Pun g 1), pear (Pyr c 1, Pyr c 3, Pyr c 4, Pyr c 5), castor bean (Ric c 1), red raspberry (Rub i 1, Rub i 3), Sesame (Ses i 1, Ses i 2, Ses i 3, Ses i 4, Ses i 5, Ses i 6, Ses i 7), yellow mustard (Sin a 1, Sin a 2, Sin a 3, Sin a 4), tomato (Sola l 1, Sola l 2, Sola l 3, Sola l 4), potato (Sola t 1, Sola t 2, Sola t 3, Sola t 4), Mung bean (Vig r 1, Vig r 2, Vig r 3, Vig r 4, Vig r 5, Vig r 6), grape (Vit v 1), Chinese date (Ziz m 1), *Anacardium occidentale* (Ana o 1.0101, Ana o 1.0102), *Apium graveolens* (Api g 1.0101, Api g 1.0201), *Daucus carota* (Dau c1.0101, Dau c1.0102, Dau c1.0103, Dau c1.0104, Dau c1.0105, Dau c1.0201), *Citrus sinensis* (Cit s3.0101, Cit s3.0102), *Glycine max* (Gly m1.0101, Gly m1.0102, Gly m3.0101, Gly m3.0102), *Lens culinaris* (Len c1.0101, Len c1.0102, Len c1.0103), *Pisum sativum* (Pis s1.0101, Pis s1.0102), *Lycopersicon sativum* (Lyc e2.0101, Lyc e2.0102), *Fragaria ananassa* (Fra a3.0101, Fra a3.0102, Fra a3.0201, Fra a3.0202, Fra a3.0203, Fra a3.0204, Fra a3.0301), *Malus domestica* (Mal d1.0101, Mal d1.0102, Mal d1.0103, Mal d1.0104, Mal d1.0105, Mal d1.0106, Mal d1.0107, Mal d1.0108, Mal d1.0109, Mal d1.0201, Mal d1.0202, Mal d1.0203, Mal d1.0204, Mal d1.0205, Mal d1.0206, Mal d1.0207, Mal d1.0208, Mal d1.0301, Mal d1.0302, Mal d1.0303, Mal d1.0304, Mal d1.0401, Mal d1.0402, Mal d1.0403, Mal d3.0101w, Mal d3.0102w, Mal d3.0201w, Mal d3.0202w, Mal d3.0203w, Mal d4.0101, Mal d4.0102, Mal d4.0201, Mal d4.0202, Mal d4.0301, Mal d4.0302), *Prunus avium* (Pm av1.0101, Pm av1.0201, Pm av1.0202, Pm av1.0203), and *Prunus persica* (Pm p4.0101, Pm p4.0201); and any variants thereof. The names of allergens associated with food are systematically named and listed according to IUIS Allergen Nomenclature Sub-Committee (see, International Union of Immunological Societies Allergen Nomenclature Sub-Committee, List of isoallergens and variants.)

In addition to food allergens, signaling polynucleotides of the present invention may detect airborne particulates/allergens and other environmental allergens. Samples that contain allergens may be obtained from plants (e.g. weeds, grasses, trees, pollens), animals (e.g., allergens found in the dander, urine, saliva, blood or other bodily fluid of mammals such as cat, dog, cow, pig, sheep, horse, rabbit, rat, guinea pig, mouse and gerbil), fungi/mold, insects (e.g., stinging insects such as bee, wasp, and hornet and chirnomidae (non-biting midges), as well as other insects such as the housefly, fruit fly, sheep blow fly, screw worm fly, grain weevil, silkworm, honeybee, non-biting midge larvae, bee moth larvae, mealworm, cockroach and larvae of *Tenibrio molitor* beetle; spiders and mites such as the house dust mite), rubbers (e.g. latex), metals, chemicals (e.g. drugs, protein detergent additives) and autoallergens and human autoallergens (e.g. Hom s 1, Hom s 2, Hom s 3, Hom s 4, Hom s 5) (see, Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants).

Examples of allergenic proteins from plants that can be detected using the compositions of the present invention include, but are not limited to, ash (Fra e 1), Japanese cypress (Cha o1, Cha o 2), sugi (Cry j1, Cry j 2), cypress (Cup a 1), common cypress (Cups 1, Cup s 3), mountain cedar (Jun a 1, Jun a 2, Jun a 3, Jun s 1), prickly juniper (Juno 4), eastern red cedar (Jun v 1, Jun v 3), sweet vernal grass (Ant o 1), saffron crocus (Cro s 1, Cro s 2), Bermuda grass (Cyn d 1, Cyn d 7, Cyn d 12, Cyn d 15, Cyn d 22w, Cyn d 23, Cyn d 24), orchard grass (Dac g 1, Dac g 2, Dac g 3, Dac g 4, Dac g 5), meadow fescue (Fes p 4), velvet grass (Hol l 1, Hol l 5), barley (Hor v 1, Hor v 5), rye grass (Lol p 1, Lol p 2, Lol p 3, Lol p 4, Lol p 11), bahia grass (Pas n 1), canary grass (Pha a 1, Pha a 5), timothy (Phl p 1, Phl p 2, Phl p 4, Phl p 5, Phl p 6, Phl p 7, Phl p 11, Phl p 12, Phl p 13), date palm (Pho d 2), Kentucky blue grass (Poa p 1, Poa p 5), rye (Sec c 1, Sec c 5, Sec c 38), Johnson grass (Sor h 1), wheat (Tri a 15, Tri a 21, Tri a 27, Tri a 28, Tri a 29, Tri a 30, Tri a 31, Tri a 32, Tri a 33, Tri a 34, Tri a 35, Tri a 39), maize (Zea m 1, Zea m 12), alder (Aln g 1, Aln g 4), redroot pigweed (Ama r 2), short ragweed (Amba 1, Amba 2, Amba 3, Amba 4, Amba 5, Amba 6, Amba 7, Amba 8, Amba 9, Amb a 10, Amb a 11), western ragweed (Amb p 5), giant ragweed (Amb t 5), mugwort (Art v 1, Art v 2, Art v 3, Art v 4, Art v 5, Art v 6), sugar beet (Beta v 1, beta v 2), European white birch (Bet v 1, Bet v 2, Bet v 3, Bet v 4, Bet v 6, Bet v 7), turnip (Bra r 5), hornbeam (Car b 1), chestnut (Cas s 1), rosy periwinkle (Cat r 1), lamb's-quarters, pigweed (Che a 1, Che a 2, Che a 3), Arabian coffee (Cof a 1, Cof a 2, Cof a 3), Hazel (Cor a 6, Cor a 10), Hazel nut (Cor a1.04, Cor a2, Cor a8), European beech (Fag s 1), ash (Fra e 1), sunflower (Hel a 1, Hel a 2), para rubber tree (Hev b 1, Hev b 2, Hev b 3, Hev b 4, Hev b 5, Hev b 6, Hev b 7, Hev b 8, Hev b 9, Hev b 10, Hev b 11, Hev b 12, Hev b 13, Hev b 14), Japanese hop (Hum j 1), privet (Lig v 1), *Mercurialis annua* (Mer a 1), olive (Ole e 1, Ole e 2, Ole e 3, Ole e 4, Ole e 5, Ole e 6, Ole e 7, Ole e 8, Ole e 9, Ole e 10, Ole e 11), *European hophornbeam* (Ost c 1), *Parietaria judaica* (Par j 1, Par j 2, Par j 3, Par j 4), *Parietaria officinalis* (Par o 1), *Plantago lanceolata* (Pal I 1), London plane tree (Pla a 1, Pla a 2, Pla a 3), *Platanus orientalis* (Pla or 1, Pla or 2, Pla or 3), white oak (Que a 1), Russian thistle (Sal k 1, Sal k 2, Sal k 3, Sal k 4, Sal k 5), tomato (Sola I 5), Lilac (Syr v 1, Syr v 5), Russian-thistle (Sal k 1), English plantain (Pla 11), *Ambrosia artemisiifolia* (Amb a8.0101, Amb a8.0102, Amb a9.0101, Amb a9.0102), *Plantago lanceolata* (Pla 11.0101, Pla 11.0102, Pla 11.0103), *Parietaria judaica* (Par j 3.0102), *Cynodon dactylon* (Cyn d1.0101, Cyn d1.0102, Cyn d1.0103, Cyn d1.0104, Cyn d1.0105, Cyn d1.0106, Cyn d1.0107, Cyn d1.0201, Cyn d1.0202, Cyn d1.0203, Cyn d1.0204), *Holcus lanatus* (Hol 11.0101, Hol 11.0102), *Lolium perenne* (Phl p1.0101, Phl p1.0102, Phl p4.0101, Phl p4.0201, Phl p5.0101, Phl p5.0102, Phl p5.0103, Phl p5.0104, Phl p5.0105, Phl p5.0106, Phl p5.0107, Phl p5.0108, Phl p5.0201, Phl p5.0202), *Secale cereale* (Sec c20.0101, Sec c20.0201), *Betula verrucosa* (Bet v1.0101, Bet v1.0102, Bet v 1.0103, Bet v 1.0201, Bet v 1.0301, Bet v1.0401, Bet v 1.0402, Bet v 1.0501, Bet v 1.0601, Bet v 1.0602, Bet v1.0701, Bet v1.0801, Bet v1.0901, Bet v1.1001, Bet v1.1101, Bet v1.1201, Bet v 1.1301, Bet v1.1401, Bet v1.1402, Bet v1.1501, Bet v1.1502, Bet v1.1601, Bet v1.1701, Bet v 1.1801, Bet v1.1901, Bet v1.2001, Bet v1.2101, Bet v1.2201, Bet v1.2301, Bet v1.2401, Bet v 1.2501, Bet v1.2601, Bet v1.2701, Bet v1.2801, Bet v1.2901, Bet v1.3001, Bet v1.3101, Bet v 6.0101, Bet v6.0102), *Carpinus betulus* (Car b1.0101, Car b1.0102, Car b1.0103, Car b1.0104, Car b1.0105, Car b1.0106, Car b1.0106, Car b1.0106, Car b1.0106, Car b1.0107, Car b1.0107, Car b1.0108, Car b1.0201, Car b1.0301, Car b1.0302), *Corylus avellana* (Cor a1.0101, Cor a1.0102, Cor a1.0103, Cor a1.0104, Cor a1.0201, Cor a1.0301, Cor a1.0401, Cor a1.0402, Cor a1.0403, Cor a1.0404), *Ligustrum vulgare* (Syr v1.0101, Syr v1.0102, Syr v1.0103), *Cryptomeria japonica* (Cry j2.0101, Cry j2.0102), and *Cupressus sempervirens* (Cup s1.0101, Cup s1.0102, Cup s1.0103, Cup s1.0104, Cup s1.0105); and any variants thereof.

Lupin is an herbaceous plant of the leguminous family belonging to the genus *Lupinus*. In Europe, lupin flour and seeds are widely used in bread, cookies, pastry, pasta, sauces, as well as in beverages as a substitute for milk or soy, and in gluten-free foods. The International Union of Immunological Societies (IDIS) allergen nomenclature subcommittee recently designated β-conglutin as the Lup an 1 allergen. (Nadal, et al., (2012) *DNA Aptamers against the Lup an 1 Food Allergen*. PLoS ONE 7(4): e35253), and more recently, a high-affinity 11-mer DNA aptamer against Lup an 1 (β-conglutin) was reported (Nadal, et al., (2013) *Probing high-affinity* 11-*mer DNA aptamer against Lup an* 1 (β-*conglutin*). Anal. Bioanal. Chem. 405:9343-9349).

Examples of allergenic proteins from mites that can be detected using the compositions of the present invention include, but are not limited to, mite (Blo t 1, Blo t 3, Blo t 4, Blot 5, Blot 6, Blot 10, Blot 11, Blot 12, Blot 13, Blot 19, Blot t 21); American house dust mite (Der f 1, Der f 2, Der f 3, Der f 7, Der f 10, Der f 11, Der f 13, Der f 14, Der f 15, Der f 16, Der f 17, Der f 18, Der f 22, Der f 24); *Dermatophagoides microceras* (house dust mite) (Der m 1); European house dust mite (Der p 1, Der p 2, Der p 3, Der p 4, Der p 5, Der p 6, Der p 7, Der p 8, Der p 9, Der p 10, Der p 11, Der p 14, Der p 15, Der p 20, Der p 21, Der p 23); *Euroglyphus maynei* (House dust mite) (Eur m 2, Eur m 2, Eur m 3, Eur m 4, Eur m 14); storage mite (Aca s 13, Gly d 2, Lep d 2, Lep d 5, Lep d 7, Lep d 10, Lep d 13, Tyr p 2, Tyr p 3, Tyr p 10, Tyr p 13, Tyr p 24), *Dermatophagoides farinae* (Der f1.0101, Der f1.0102, Der f1.0103, Der f1.0104, Der f1.0105, Der f2.0101, Der f2.0102, Der f2.0103, Der f2.0104, Der f2.0105, Der f2.0106, Der f2.0107, Der f2.0108, Der f2.0109, Der f2.0110, Der f2.0111, Der f2.0112, Der f2.0113, Der f2.0114, Der f2.0115, Der f2.0116, Der f2.0117), *Dermatophagoides pteronyssinus* (Der p1.0101, Der p1.0102, Der p1.0103, Der p1.0104, Der p1.0105, Der p1.0106, Der p1.0107, Der p1.0108, Der p1.0109, Der p1.0110, Der p1.0111, Der p1.0112, Der p1.0113, Der p1.0114, Der p1.0115, Der p1.0116, Der p1.0117, Der p1.0118, Der p1.0119, Der p1.0120, Der p1.0121, Der p1.0122, Der p1.0123, Der p2.0101, Der p2.0102, Der p2.0103, Der p2.0104, Der p2.0105, Der p2.0106, Der p2.0107, Der p2.0108, Der p2.0109, Der p2.0110, Der p2.0111, Der p2.0112, Der p2.0113), Euroglyphus maynei (Eur m2.0101, Eur m2.0102), *Lepidoglyphus destructor* (Lep d2.0101, Lep d2.0101, Lep d2.0101, Lep d2.0102, Lep d2.0201, Lep d2.020) and *Glycyphagus domesticus* (Gly d2.0101, Gly d2.0201); and any variants thereof.

Examples of allergenic proteins from animals that can be detected using the compositions of the present invention include, but are not limited to, domestic cattle (Bos d 2, Bos d 3, Bos d 4, Bos d 5, Bos d 6, Bos d 7, Bos d 8), dog (Can f 1, Can f 2, Can f 3, Can f 4, Can f 5, Can f 6), domestic horse (Equ c 1, Equ c 2, Equ c 3, Equ c 4, Equ c 5), cat (Fel d 1, Fel d 2, Fel d 3, Fel d 4, Fel d 5w, Fel d 6w, Fel d 7, Fel d 8), mouse (Mus m 1), guinea pig (Cav p 1, Cav p 2, Cav p 3, Cav p 4, Cav p 6), rabbit (Ory c 1, Ory c 3, Ory c 4) rat (Rat n 1), *Bos domesticus* (Bos d 2.0101, Bos d 2.0102, Bos d 2.0103) and *Equus caballus* (Equ c2.0101, Equ c 2.0102); and any variants thereof.

Examples of allergenic proteins from insects that can be detected using the compositions of the present invention include, but are not limited to, yellow fever mosquito (Aed a 1, Aed a 2, Aed a 3), Eastern hive bee (Api c 1), giant honeybee (Api d 1), honey bee (Api m 1, Api m 2, Api m 3, Api m 4, Api m 5, Api m 6, Api m 7, Api m 8, Api m 9, Api m 10, Api m 11, Api m 12), pigeon tick (Arg r 1), German cockroach (Bla g 1, Bla g 2, Bla g 3, Bla g 4, Bla g 5, Bla g 6, Bla g 7, Bla g 8, Bla g 11), bumble bee (Bom p 1, Bom p 4, Bom t 1, Bom t 4), silk moth (Bomb m 1), midge (Chi k 10, Chi t 1, Chi t 1.01, Chi t 2, Chi t 2. 0101, Chi t 2. 0102, Chi t 3, Chi t 4, Chi t 5, Chi t 6, Chi t 6. 01, Chi t 7, Chi t 8, Chi t 9), cat flea (Cte f 1, Cte f 2, Cte f 3), yellow hornet (Dol a 5), white face hornet (Dol m 1, Dol m 2, Dol m 5), biting midge (Fort 1, Fort 2), Savannah Tsetse fly (Glo m 5), Asian ladybeetle (Har a 1, Har a 2), silverfish (Lep s 1), booklouse (Lip b 1), Australian jumper ant (Myr p 1, Myr p 2, Myr p 3), American cockroach (Per a 1, Per a 3, Per a 6, Per a 7, Per a 9, Per a 10), Indian meal moth (Plo i 1, Plo i 2), wasp (Pol a 1, Pol a 2, Pol a 5, Pole 1, Pole 4, Pole 5, Pol f 5, Pol g 1, Pol g 5, Pol m 5, Polyp 1, Polys 5, Ves vi 5), Mediterranean paper wasp (Pol d 1, Pol d 4, Pol d 5), tropical fire ant (Sol g 2, Sol g 3, Sol g 4), *Solenopsis invicta* (red imported fire ant) (Sol I 1, Sol I 2, Sol I 3, Sol I 4), black fire ant (Sol r 2, Sol r 3), Brazilian fire ant (Sol s 2, Sol s 3), horsefly (Tab y 1, Tab y 2, Tab y 5), pine processionary moth (Tha p 1, Tha p 2), California kissing bug (Tria p 1), European hornet (Vesp c 1, Vesp c 5), *Vespa magnifica* (hornet) (Vesp ma 2, Vesp ma 5), *Vespa mandarinia* (Giant asian hornet) (Vesp ml, Vesp m 5), yellow jacket (Ves f 5, Ves g 5, Ves m 1, Ves m 2, Ves m 5), *Vespula germanica* (yellow jacket) (Ves p 5), *Vespula squamosa* (Yellow jacket) (Ves s 1, Ve s s5), *Vespula vulgaris* (Yellow jacket) (Ves v 1, Ves v 2, Ves v 3, Ves v 4, Ves v 5, Ves v 6), *Blattella germanica* (Bla g 1.0101, Bla g 1.0102, Bla g 1.0103, Bla g 1.02, Bla g 6.0101, Bla g 6.0201, Bla g 6.0301), *Periplaneta Americana* (Per a1.0101, Per a1.0102, Per a1.0103, Per a1.0104, Per a1.02, Per a3.01, Per a3.0201, Per a3.0202, Per a3.0203, Per a7.0101, Per a7.0102), *Vespa crabo* (Ves pc 5.0101, Ves pc 5.0101), *Vespa mandarina* (Vesp m 1.01, Vesp m 1.02); and any variants thereof.

Examples of allergenic proteins from fungi/mold that can be detected using the signaling polynucleotides and assays of the present invention include, but are not limited to, *Alternaria alternata* (*Alternaria* rot fungus) (Alt a 1, Alt a 3, Alt a 4, Alt a 5, Alt a 6, Alt a 7, Alt a 8, Alt a 10, Alt a 12, Alt a 13), *Aspergillus flavus* (fungus) (Asp fl 13), *Aspergillus fumigatus* (fungus) (Asp f 1, Asp f 2, Asp f 3, Asp f 4, Asp f 5, Asp f 6, Asp f 7, Asp f 8, Asp f 9, Asp f 10, Asp f 11, Asp f 12, Asp f 13, Asp f 15, Asp f 16, Asp f 17, Asp f 18, Asp f 22, Asp f 23, Asp f 27, Asp f 28, Asp f 29, Asp f 34), *Aspergillus niger* (Asp n 14, Asp n 18, Asp n 25), *Aspergillus oryzae* (Asp o 13, Asp o 21), *Aspergillus versicolor* (Asp v 13), *Candida albicans* (Yeast) (Cand a 1, Cand a 3), *Candida boidinii* (Yeast) (Cand b 2), *Cladosporium cladosporioides* (Cla c 9, Cla c 14), *Cladosporium herbarum* (Cla h 2, Cla h 5, Cla h 6, Cla h 7, Cla h 8, Cla h 9, Cla h 10, Cla h 12), *Curvularia lunata* (Synonym: *Cochliobolus lunatus*) (Cur l 1, Cur l 2, Cur l 3, Cur l 4), *Epicoccum purpurascens* (Soil fungus) (Epi p 1), *Fusarium culmorum* (N.A.) (Fus c 1, Fus c 2), *Fusarium proliferatum* (Fus p 4), *Penicillium brevicompactum* (Pen b 13, Pen b 26), *Penicillium chrysogenum* (Pen ch 13, Pen ch 18, Pen ch 20, Pen ch 31, Pen ch 33, Pen ch 35), *Penicillium citrinum* (Pen c 3, Pen c 13, Pen c 19, Pen c 22, Pen c 24, Pen c 30, Pen c 32), *Penicillium crustosum* (Pen cr 26), *Penicillium oxalicum* (Pen o 18), *Stachybotrys chartarum* (Sta c 3), *Trichophyton rubrum* (Tri r 2, Tri r 4), *Trichophyton tonsurans* (Tri t 1, Tri t 4), *Psilocybe cubensis* (Psi c 1, Psi c 2), Shaggy cap (Cop c 1, Cop c 2, Cop c 3, Cop c 5, Cop c 7), *Rhodotorula mucilaginosa* (Rho m 1, Rho m 2), *Malassezia furfur* (Malaf2, Malaf3, Malaf4), *Malassezia sympodialis* (Malas1, Malas5, Malas6, Malas7, Malas8, Malas9, Malas10, Malas11, Malas12, Malas13) and *Alternaria alternate* (Alt a1.0101, Alt a1.0102); and any variants thereof.

Examples of additional allergens include, but are not limited to, Nematode (Ani s 1, Ani s 2, Ani s 3, Ani s 4), worm (Asc s 1), soft coral (Den n 1), rubber (Latex) (Hev b 1, Hev b 2, Hev b 3, Hev b 5, Hev b 6, Hev b 7, Hev b 8, Hev b 9, Hev b 10, Hev b 11, Hev b 12, Hev b 13), obeche (Trip s 1) and *Heveabrasiliensis* (Hev b6.01, Hev b6.0201, Hev b6.0202, Hev b6.03, Hev b8.0101, Hev b8.0102, Hev b8.0201, Hev b8.0202, Hev b8.0203, Hev b8.0204, Hey b10.0101, Hev b10.0102, Hev b10.0103, Hev b11.0101, Hev b11.0102); and any variants thereof.

In some embodiments, SPNs and compositions of the present invention may be used in a hospital for clinical food allergy or allergy test and to identify food/allergen(s) to which a patient is allergic. In addition, SPNs and compositions of the present invention may be used as a carry-on tester for people who have food/environmental allergy, for example at home to test commercial food, or at restaurant to check dishes they ordered. The food sample could be fresh food, frozen food, cooled food or processed food containing animal derived meat and/or vegetables.

Other Target Molecules

In some embodiments, SPNs and compositions of the present invention may detect other target molecules, including but not limited to, pathogens from a pathogenic microorganism in a sample, such as bacteria, yeasts, fungi, spores, viruses or prions; disease proteins (e.g., biomarkers for diseases diagnosis and prognosis); pesticides and fertilizers remained in the environment; and toxins. In other embodiments, SPNs and compositions of the present invention may bind to non-protein targets such as minerals and small molecules (e.g., antibiotics).

Applications

In accordance with the present invention, detection molecules, signaling polynucleotides (SPNs), compounds and compositions of the present invention may be used to, in a broad concept, detect any proteins in a sample in a large variety of applications, such as food safety, diagnostic and prognostic tests in civilian and battlefield settings, environmental monitoring/control, and military use for detection of biological weapons. In even broader applications, the detection molecules, signaling polynucleotides (SPNs), compounds and compositions of the present invention may be used to detect any substances to which nucleic acid-based detection molecules bind, such as minerals in water.

The applications in food safety control may include, but are not limited to, detecting and monitoring food contaminants (e.g., pathogens and toxins), food quality (e.g., nutrients), diet supplements, and food allergens. The applications in a battle field setting may include, but are limited to, testing of antibiotics and biological drugs, biological weapons, infectious diseases monitoring and food safety.

Various methods and assays may be used in combination with the detection molecules, signaling polynucleotides, compounds and compositions of the present invention; the choice may depend on the application field.

Detection Methods and Assays: Food Allergens

In some embodiments, analytical assays and methods for detecting various allergens (e.g., food allergens) in samples are provided. Assays and methods provided can detect the presence or absence of an allergen of interest in a sample, and/or determine the amount of the allergen in a sample.

In some embodiments, methods for detecting one or more allergens in a test sample, such as a food sample, comprise the steps (a) obtaining a test sample suspected of containing an allergen; (b) processing the test sample and extracting proteins from the processed sample using an extraction buffer; (c) mixing the protein extraction of step (b) with a SPN that specifically binds to the allergen; (d) activating the sample and SPN mixture by means of an energy excitation; and (e) visualizing the interaction between the SPN and the allergen protein and detecting the absence or presence of the allergen in the test sample. In some embodiments, a light-emitting diode (LED) light may be used as an excitation means.

Sample Processing and Extraction Buffer

The ability of a detection assay and method to detect allergen proteins in a test sample is affected by the efficiency with which these proteins are extracted from the samples, in addition to the efficiency with which the detection molecules used in the present invention to detect these proteins in the sample extract. In some embodiments, samples are processed and allergen proteins are extracted to ensure a fast, reliable and sensitive detection assay. The sample size and weight, extraction solution and extraction process may be optimized for an effective and non-destructive reaction. Any mechanisms that can break samples such as cutting, grinding, homogenization and filtration may be used, alone or in combination, to process a sample.

In some embodiments, a universal protein extraction buffer may be used to retrieve enough target proteins (e.g. allergens) (minimum 2 mg/ml total protein) for analysis from any food matrix. In some embodiments, the formulation of the universal protein extraction buffer can extract the protein at room temperature and in minimal time. In some aspects, allergen proteins may be extracted in less than about 2 minutes, or less than about 1 minute, or less than about 30 seconds. The buffer may need to be incorporated with an extraction protocol that will include food sampling, homogenization and filtration. The extraction protocol may be implemented in a way that is efficient and repeatable over time and in different food matrices. This universal formulation will be clinically relevant as to try to minimally effect the food tested and only sample approximately 0.5 g of food, allowing to detect traces of allergens their concentration will be minimal in the sample. This optimized protein extraction process will provide a fast, accurate and universal protocol that allows detection of an allergen in any food matrix.

This universal extraction buffer can maximize protein extraction and allergen retrieval. The universal extraction buffer will be applicable to any allergen and to all foods (e.g. pre-processed or post-processed). Additionally, the universal extraction buffer can improve signaling polynucleotides (SPNs) binding affinity, minimize non-specific binding and increase signal to noise ratio.

Allergen Detection Assays

In some embodiments, compositions, compounds and signaling polynucleotides of the present invention may be used to replace antibodies as an alternative molecular recognition element in enzyme-linked immunosorbent assay (ELISA). The application of aptamer based signaling polynucleotides in ELISA gives rise to an ELISA-derived assay called enzyme-linked apta-sorbent assay (ELASA). As with the ELISA method, ELASA can be used in several different configurations, including direct, indirect, and sandwich assays (Toh et al., Biosens. Bioelectron, 2015, 64, 392-403, the content of which is incorporated herein by reference in its entirety.)

In some embodiments, compositions, compounds and signaling polynucleotides of the present invention may be used in a real-time apta-PCR for detection of a target protein in a sample. In this assay, the target in the test sample and immobilized same target will compete for aptamer binding. Following competition, any aptamer bound to the immobilized target protein can be heat-eluted and quantitatively amplified using real-time PCR. Aptamers used for this assay can be label-free (Pinto et al., *Anal-Bioanal Chem.*, 2014, 406(2), 515-524; and Svobodova et al., *Food Chem.*, 2014, 165, 419-423; the content of each of which is incorporated herein in its entirety.)

In some embodiments, allergen detection assays may depend on fluorescence emission signal from fluorescence resonance energy transfer (FRET). Signaling polynucleotides (SPNs) is labeled with fluorophore at the ends of the sequences. The specific interaction with a target induces a change in the bi-aptameric structure resulting in an increase in fluorescence emission. The method is highly specific and sensitive.

In certain embodiments, one or more signaling polynucleotides (SPNs) may be used, depending on the nature of the food matrixes. Some food contains several allergenic proteins, e.g., at least eight peanut proteins, such as Ara h1 and Ara h2, can potentially cause an immunological response. In such case, more than one signaling polynucleotides (SPNs) against more than one allergenic protein may be used in a mixed cocktail for detecting the absence or presence of peanut. In other aspects, some food matrixes such as fish, shellfish and mollusks, contain only one major allergenic protein. One or more SPNs that specifically bind to this major allergen protein may be used for allergen detection.

In order to provide an accurate and reliable detection result in an allergen detection assay, total proteins extracted from a test sample are measured. The total proteins extracted from a test sample may be determined using any protein assays known to a skilled artisan in the field, e.g., bicinchoninic acid assay (BCA). In some aspects, a protein indication molecule (e.g., Pyrogalbl Red Molybdate, PRM) is used to determine the total protein. Any signal detected from the detection molecule-allergen interaction will be nominated by the total protein measurement.

In some embodiments, allergen detection assays and methods of the present invention provide a calibration standard (i.e. calibration curves) for a particular allergen and a SPN used. The calibration standard of a particular allergen protein may be generated from a raw or processed material that contains such allergen, or a purified allergen.

In some embodiments, allergen detection assays and methods of the present invention can detect a lower concentration of allergen in a food sample. The sensitivity of nucleic acid aptamers makes it possible to detect the presence of an allergen as low as 0.0001 ppm. In some aspects, the concentration or mass of allergen that can be detected may range from 0.001 ppm to 5 ppm, or from 0.001 ppm to 0.1 ppm, or from 0.1 ppm to 3 ppm, or from 1 ppm to 5 ppm, or from 5 ppm to 10 ppm. In some aspects, the concentration or mass of allergen in a food sample that can be detected may be 0.001 ppm, 0.002 ppm, 0.003 ppm, 0.004 ppm, 0.005 ppm, 0.006 ppm, 0.007 ppm, 0.008 ppm, 0.009 ppm, 0.01 ppm, 0.02 ppm, 0.03 ppm, 0.04 ppm, 0.05 ppm, 0.06 ppm, 0.07 ppm, 0.08 ppm, 0.09 ppm, 0.1 ppm, 0.2 ppm, 0.3 ppm, 0.4 ppm, 0.5 ppm, 0.6 ppm, 0.7 ppm, 0.8 ppm, 0.9 ppm, 1.0 ppm, 1.5 ppm, 2 ppm, 2.5 ppm, 3 ppm, 3.5 ppm, 4 ppm, 4.5 ppm, 5 ppm or 10 ppm.

In some embodiments, allergen detection assays and methods of the present invention may complete the implementation in less than 5 minutes. In some aspects, the assay time may be from about 1 minute to about 5 minutes, about 1 minute to about 3 minute, about 2 minutes to about 10 minutes, about 5 minutes to about 10 minutes. In other aspects, the assay time may last less than 1 min, 2 min 3 min, 4 min, 5 min, 6 min, 7 min, 8 min, 9 min, or 10 min. In further other aspects, the assay time may last less than about 10 seconds, about 15 seconds, about 20 seconds, about 25 seconds, about 30 seconds, about 35 seconds, about 40 seconds, about 45 seconds, about 50 seconds, about 55 seconds or about 60 seconds.

Detection System and Display Platform

Methods and systems used to detect and display aptamer and protein interaction may be used to display the detection results.

A commonly used method in the field is the use of electrochemical indicators which detect mass and charge transfer during aptamer and target interaction. According to this method, Aptamers are loaded to an electrode and an electrochemical indicator is bound to a target of interest. Electrochemical indicators may include, but are not limited to, methylene blue (MB).

Some non-limiting examples of methods for detection of aptamer-target interaction include an assay for the direct detection of cancer cells using aptamer-conjugated gold nanoparticles (ACGNPs) selective for cell surface molecules on CCRF-CEM cells (CCL-119 T-cell, human acute lymphoblastic leukemia) and Ramos cells (CRL-1596, B-cell, human Burkitt's lymphoma) (Medley, et al., *Gold Nanoparticle-Based Colorimetric Assay for the Direct Detection of Cancerous Cells*. Anal. Chem. 2008, 80:1067-1072); the use of aptamer-linked gold nanoparticles (AuNPs) that undergo fast disassembly into red dispersed nanoparticles upon binding of target analytes (Lu, et al. Chapter 14: Nanoparticles/Dip Stick, in *Nucleic Acid and Peptide Aptamers: Methods and Protocols*, Gunter Mayer (ed.). 535:223-239); and a differential pulse voltammetry (DPV)-based biosensor employing aptamer-AuNP conjugates as the sandwich-amplification element for the ultrasensitive detection of IgE in human serum (over a range 1-10,000 ng/mL with an LOD as low as 0.52 ng/mL) (Wang, et al., *Aptamer-Au NPs conjugates-accumulated methylene blue for the sensitive electrochemical immunoassay of protein*, Talanta, 15 Apr. 2010, 81(1-2):63-67).

However, at least one disadvantage shared by many electrochemical biosensors is the off-line nature of the measurements, requiring long incubation times with analyte solution, rather than real-time detection (Pilloli, et al., *Advances in biosensor development based on integrating nanotechnology and applied to food-allergen management*. Trends in Analytical Chemistry, June 2013, 47:12-26).

In accordance with the present invention, an optical assembly may be used to detect the interaction between a SPN and a target allergen. The optical assembly may comprise a light emitting diode (LED) that provides light of an excitation wavelength appropriate to excite the fluorophore of the signaling polynucleotides. The fluorescence emitted from the fluorophores of the SPNs may be filtered and only the wavelength(s) of interest is transmitted. A means then may be used to process and convert the fluorescence signals to useful readouts (i.e. digital signals).

The detection result from the present assay may be displayed in a platform that a user can easily read such as a display window. In one embodiment, it may be a platform application in a cellphone (Coskun et al., *A personalized food allergen testing platform on a cellphone*, Lab Chip., 2013, 13(4), 636-640; the content of which is incorporated herein by reference in its entirety.)

Formulations, Packaging, Kits, Devices and Systems
Formulations:

Detection molecules, compounds, signaling polynucleotides of the present invention may be formulated following standard procedures. In some embodiments, detection molecules, SPNs of the present invention may be formulated in a solution which favors the interaction between the detection molecules and the allergen.

Packaging:

Formulations and/or compositions of detection molecules, signaling polynucleotides of the present invention can be packaged for use in a variety of pharmaceutically or diagnostically acceptable containers using any acceptable container closure, as the formulations are compatible with PVC-containing and PVC-free containers and container closures. Examples of acceptable containers include, but are not limited to, ampules and pre-filled syringes, cartridges and the like.

Alternatively, the formulation may contain lyophilized aptamer in one compartment of an admix bag and an acceptable solvent in a separate compartment of the admix bag such that the two compartments may be mixed together prior to administration to a patient. Acceptable containers are well known in the art and commercially available. Preferably, the formulations are stored in a Type 1 glass vial with a butyl rubber stopper. The formulations in liquid form may be stored in a refrigerated environment. Alternatively, the lyophilized formulations may be stored at room temperature, or refrigerated or frozen.

Preferably, the formulations are sterile. A "sterile" formulation, as used herein, means a formulation that has been brought to a state of sterility and has not been subsequently exposed to microbiological contamination, i.e., the container holding the sterile composition has not been compromised. Sterile compositions are generally prepared by pharmaceutical manufacturers in accordance with current Good Manufacturing Practice ("cGMP") regulations of the U.S. Food and Drug Administration.

In some embodiments, sterile pharmaceutical formulations can be prepared using aseptic processing techniques. Sterility is maintained by using sterile materials and a controlled working environment. All containers and apparatus are sterilized, preferably by heat sterilization, prior to filling. Then, the container is filled under aseptic conditions, such as by passing the composition through a filter and filling the units. Therefore, the formulations can be sterile filled into a container to avoid the heat stress of terminal sterilization.

In some embodiments, the formulations are terminally sterilized using moist heat. Terminal sterilization can be used to destroy all viable microorganisms within the final, sealed container containing the pharmaceutical formulation. An autoclave is typically used to accomplish terminal heat-sterilization of drug products in their final packaging. Typical autoclave cycles in the pharmaceutical industry to achieve terminal sterilization of the final product are 121° C. for at least 10 minutes.

Kits:

Detection molecules, compounds and compositions of the present invention may be combined with other ingredients or reagents or prepared as components of kits or other retail products for commercial sale or distribution. The kit will contain the compound or composition, along with instructions regarding administration and/or use of the kit. The kit may also contain one or more of the following: a syringe, a bag or bottle.

Devices and Systems:

The signaling polynucleotides, compounds and compositions of the present invention may be used in any allergen detection devices and systems. Some non-limiting examples include lateral flow devices (LFD), microfluidic chips (U.S. Pat. No. 8,617,903), portable detection devices/systems described in the commonly owned U.S. patent application No. 62/133,632 filed on Mar. 16, 2015 and the cartridge as described in the commonly owned PCT patent application NO.: PCT/US14/62656 filed on Oct. 28, 2014, each of which is incorporated herein by reference in its entirety.

Definitions

At various places in the present specification, substituents of compounds of the present disclosure are disclosed in groups or in ranges. It is specifically intended that the present disclosure include each and every individual subcombination of the members of such groups and ranges. The following is a non-limiting list of term definitions.

About: As used herein, the term "about" when referring to a measurable value such as an amount of weight, time, dose, etc. is meant to encompass variations of ±20% or ±10%, more preferably ±5%, even more preferably ±1%, and still more preferably ±0.1% from the specified amount, as such variations are appropriate to perform the disclosed method.

Activity: As used herein, the term "activity" refers to the condition in which things are happening or being done. Compositions of the invention may have activity and this activity may involve the binding to a target molecule.

Allergen: as used herein, the term "allergen" means a compound, substance or composition that causes, elicits or triggers and immune reaction in a subject. As such, allergens are typically referred to as antigens. An allergen is typically a protein or a polypeptide.

Allergen detection molecule: As used herein, the term "an allergen detection molecule" refers to Any molecule which is capable of, or does, interact with and/or bind to one or more allergens in a way that allows detection of such allergen in a sample is referred to herein as an "allergen detection molecule" or "detection molecule".

Binding affinity: As used herein, the term "binding affinity" refers to the tendency of a detection molecule (e.g., aptamer) to bind or not bind a target (e.g., allergen) and describes the measure of the strength of the binding or affinity of the detection molecule to bind the target.

Biomolecules As used herein, the term "biomolecule" is any natural molecule which is amino acid-based, nucleic acid-based, carbohydrate-based or lipid-based, and the like.

Complementary and substantially complementary: As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100% complementarity refers to the situation in which each nucleotide unit of one polynucleotide strand can form hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form hydrogen bond with each other, the polynucleotide strands exhibit 10% complementarity. In the same example, if 18 base pairs on each strand can form hydrogen bonds with each other, the polynucleotide strands exhibit 90% complementarity.

Detection: As used herein, the term "detection" means an extraction of a particular target protein from a mixture of many non-target proteins, indicating the absence, presence, and/or amount of a target protein from a mixture of many non-target proteins.

Detectable label: As used herein, "detectable label" refers to one or more markers, signals, or moieties which are attached, incorporated or associated with another entity, which markers, signals or moieties are readily detected by methods known in the art including radiography, fluorescence, chemiluminescence, enzymatic activity, absorbance, immunological detection and the like. Detectable labels may include radioisotopes, fluorophores, chromophores, enzymes, dyes, metal ions, ligands, biotin, avidin, streptavidin and haptens, quantum dots, polyhistidine tags, myc tags, flag tags, human influenza hemagglutinin (HA) tags and the like. Detectable labels may be located at any position in the entity with which they are attached, incorporated or associated. For example, when attached, incorporated in or associated with a peptide or protein, they may be within the amino acids, the peptides, or proteins, or located at the N- or C-termini.

Including: As used herein, the term "including" refers to "including but not limited to". "Including" and "including but not limited to" are used interchangeably.

Interaction: As used herein, the term "interaction" refers to a kind of action that occurs as two or more molecules have effect upon one another. In the context of the present invention, an interaction between a detection molecule and a target affects the structure of the detection molecule and such effect will generate energetic changes that can be visualized.

Pathogen: As used herein, the term "pathogen" means any disease-producing agent (especially a virus or bacterium or other microorganism).

Polynucleotide: As used herein, the term "polynucleotide" refers to nucleobase polymers or oligomers in which the nucleobases are connected by sugar phosphate linkages (sugar-phosphate backbone). Exemplary poly- and oligonucleotides include polymers of 2' deoxyribonucleotides (DNA) and polymers of ribonucleotides (RNA). A polynucleotide may be composed entirely of ribonucleotides, entirely of 2' deoxyribonucleotides or combinations thereof.

Polynucleotide variants: As used herein, the term "polynucleotide variants" refers to molecules with some differences in their nucleic acid sequences as compared to a native or starting sequence.

ppm: As used herein, the term "ppm" is an abbreviation of parts per million. ppm is a value that represents the part of a whole number in units of 1/1000000. ppm is dimensionless quantity, a ratio of 2 quantities of the same unit. For example: mg/kg. One ppm is equal to 1/1000000 of the whole: 1 ppm=1/1000000=0.000001=1×10$^{-6}$. ppm herein is used to measure chemical (protein) concentration, usually in a solution. Solute concentration of 1 ppm is solute concentration of 1/1000000 of the solution. The concentration C in ppm is calculated from the solute mass $m_{solute}$ in milligrams and the solution mass $m_{solution}$ in milligrams: $C_{(ppm)}$= 1000000×$m_{solute}/(n_{solution}+m_{solute})$.

Sample: As used herein, the term "sample" refers to any composition that might contain a target of interest to be analyzed including, but not limited to, biological samples obtained from subjects (including humans and animals as detailed below), samples obtained from the environment for example soil samples, water samples, agriculture samples (including plant and crop samples), or food samples. Food samples may be obtained from fresh food, processed/cooked food or frozen food.

Sensitivity: As used herein, the term "sensitivity" means the ability of a detection molecule to bind to a target molecule.

Specifically bind(s): As used herein, the term: specifically bind(s)" means that a detection molecule (e.g., aptamer) reacts or associates more frequently, more rapidly, with greater duration and/or with greater affinity with a particular target such as an allergen protein than it does with alternative targets. For example, an aptamer that specifically binds to an allergen protein binds that protein or a fragment thereof with greater affinity, avidity, more readily, and/or with greater duration than it binds to unrelated protein and/or the fragments thereof. It is also understood by an artisan by this definition, for example, a detection molecule (e.g., aptamer) that specifically binds to a first target may or may not specifically bind to a second target. As such, "specific binding" does not necessarily require exclusive binding or non-detectable binding of another molecule, this is encompassed by the term "selective binding". Generally, but not necessarily, reference to binding means specific binding. The specificity of binding is defined in terms of the comparative dissociation constants (Kd) of the aptamer for target as compared to the dissociation constant with respect to the aptamer and other materials in the environment or unrelated molecules in general. Typically, the Kd for the aptamer with respect to the target will be 2-fold, 5-fold, or 10-fold less than the Kd with respect to the target and the unrelated material or accompanying material in the environment. Even more preferably, the Kd will be 25-fold, 50-fold, 75-fold, 100-fold, 150 fold or 200-fold less.

Target: as used herein, the term "target" and "target molecule" refers to a molecule which may be found in a tested sample and which is capable of binding to a detection molecule such as an aptamer or an antibody.

Universal buffer: As used herein, the term "universal buffer" refers to a buffer that may be used for a variety of samples.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

EXAMPLES

Example 1: Design of Aptamers as Signaling Polynucleotides

In this proof-of-concept example, two previously known aptamer sequences were used to design three different signaling polynucleotides. An aptamer against the Ara h 1 protein allergen is described by Tran et al. in *Selection of aptamers against Ara h 1 protein for FO-SPR biosensing of peanut allergens in food matrices*. Biosensors and Bioelectronics, 2013, 43, 245-251 (incorporated herein by reference in entirety). The sequence of this aptamer is shown below.

(SEQ ID NO: 1)
5'CGCACATTCCGCTTCTACCGGGGGGGTCGAGCTGAGTGGATGCGAATC
TGTGGGTGGGCCGTAAGTCCGTGTGTGCGAA3'

The original aptamer of SEQ ID NO: 1 was modified to add a 5'-T residue to improve the functioning of the fluorophore-quencher pair. Fluorescein was then linked to the 5'-T residue as shown below.

(SEQ ID NO: 2)
5'FluoresceinTCGCACATTCCGCTTCTACCGGGGGGGTCGAGCTGAG
TGGATGCGAATCTGTGGGTGGGCCGTAAGTCCGTGTGTGCGAA3'

A 9-nucleotide linker with a 3'-DABCYL quencher was designed as shown below to be complementary to the first ten residues of the 5'-end of the T-modified aptamer of SEQ ID NO.: 2.
3'DABCYLAGCGTGTAAS' (SEQ ID NO.: 3)

The 9-nucleotide linker (SEQ ID NO: 3) was then annealed to the 5'-end of the main modified anti-peanut allergen aptamer sequence (SEQ ID NO: 2) to bring the fluorescein fluorophore into proximity with the DABCYL quencher moiety. The structure of the assembled signaling polynucleotide for detection of peanut allergen Ara h 1 is shown below.

```
                    3'DABCYLAGCGTGTAA5' (SEQ ID NO.: 3)
                       ||||||||||
5-FluoresceinTCGCACATTCCGCTICTACCGGGGGGGTCGAGCTGAG
TGGATGCGAATCTGTGGGTGGGCCGTAAGTCCGTGTGTGCGAA3' (SEQ ID NO.: 2)
```

The signaling polynucleotide prepared from annealing SEQ ID Nos.: 2 and 3 is a dimeric entity herein designated SPN-A*. The secondary structure of SPN-A* is shown in FIG. 1. The arrangement of the components of the signaling polynucleotide 200 (SEQ ID NO.: 2) are core sequence 202 (SEQ ID NO.: 1), fluorophore 204, quencher 206 and linker sequence 208 (SEQ ID NO.: 3).

In a similar manner, a signaling polynucleotide was designed based upon the sequence of an aptamer against egg white lysozyme described by Tran et al. in *Selection and Characterization of DNA Aptamers for Egg White Lysozyme*. Molecules 2010, 15(3), 1127-1140 (incorporated herein by reference in entirety). The sequence of this aptamer is shown below.

```
                                             (SEQ ID NO: 4)
     5'GCAGCTAAGCAGGCGGCTCACAAAACCATTCGCATGCGGC3'
```

The original aptamer of SEQ ID NO: 4 was modified to add a 5'-T residue to improve the functioning of the fluorophore-quencher pair. Fluorescein was then linked to the 5'-T residue as shown below.

```
                                             (SEQ ID NO: 5)
5'FluoresceinTGCAGCTAAGCAGGCGGCTCACAAAACCATTCGCATG
CGGC3'
```

A 10-nucleotide linker with a 3'-DABCYL quencher was designed as shown below to be complementary to the first ten residues of the 5'-end of the T-modified aptamer of SEQ ID NO: 5.

```
                                             (SEQ ID NO: 6)
                    3'DABCYLACGTCGATTC5'
```

The 10-nucleotide linker (SEQ ID NO: 6) was then annealed to the 5'-end of the main modified anti-lysozyme aptamer sequence (SEQ ID NO: 5) to bring the fluorescein fluorophore into proximity with the DABCYL quencher moiety. The structure of the assembled signaling polynucleotide for detection of lysozyme is shown below.

```
           3'DABCYLACGTCGATTC5' (SEQ ID NO.: 6)
              ||||||||||||
5-FluoresceinTGCAGCTAAGCAGGCGGCTCACAAAACCATTCGCAT
GCGGC3' (SEQ ID NO.: 5)
```

Figure 3:
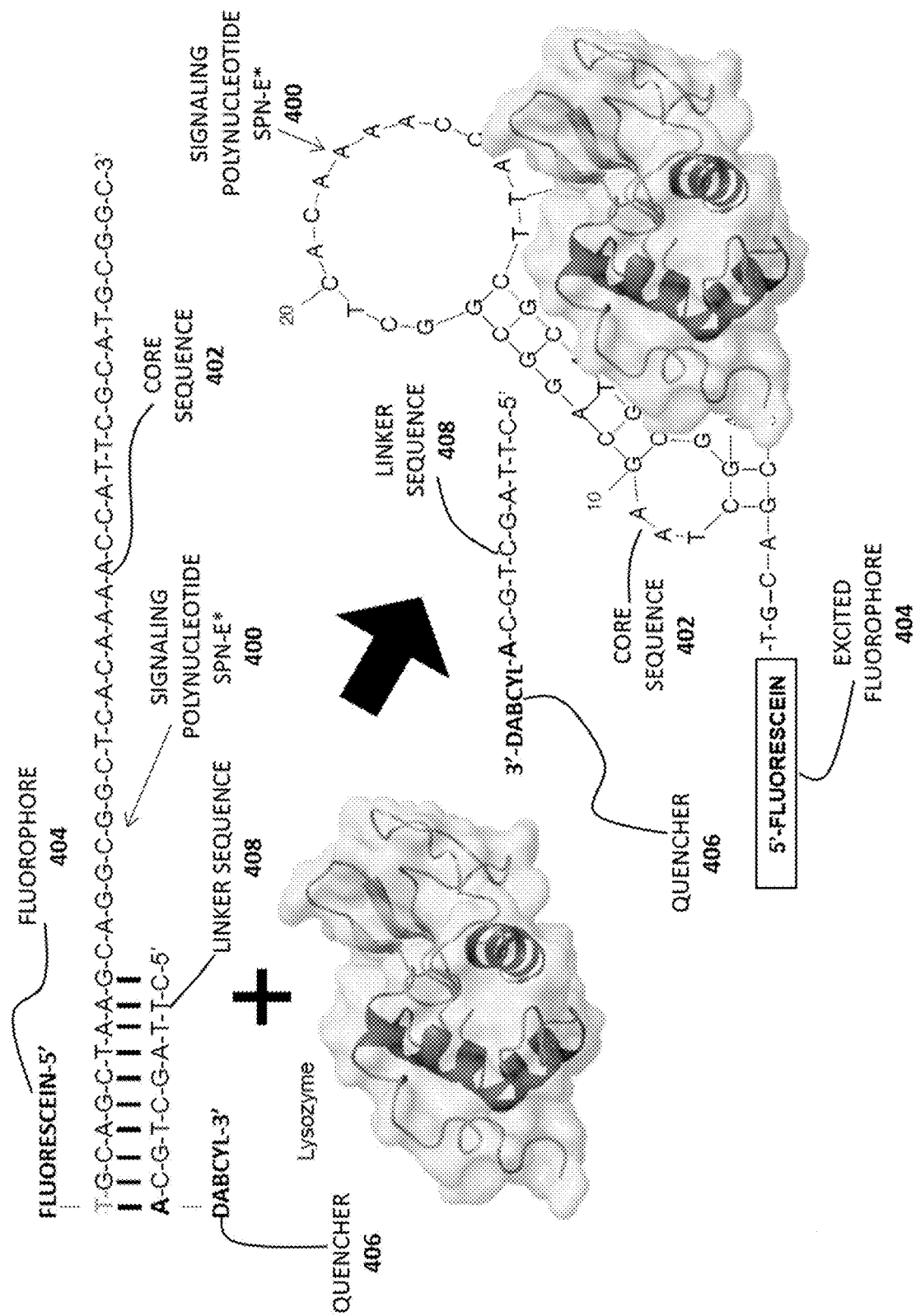
FIG. 3 shows a reaction between a detection molecule represented by a dimeric signaling polynucleotide SPN-E* 400 (including an annealed linker sequence 408 (SEQ ID NO.: 6)) with its target molecule lysozyme. Also shown are the aptamer core sequence 402 (SEQ ID NO.: 4), the fluorophore 404 and the quencher 406.

The dimeric signaling polynucleotide prepared from SEQ ID Nos.: 5 and 6 is herein designated SPN-E*. A reaction between SPN-E* and lysozyme is shown schematically in FIG. 3. The arrangement of the components of the signaling polynucleotide SPN-E* 400 (SEQ ID NO.: 5) are core sequence 402 (SEQ ID NO.: 4), fluorophore 404, quencher 406 and linker sequence 408 (SEQ ID NO.: 6). It is seen that binding of lysozyme disrupts the hairpin structure and causes the fluorophore 404 to move away from the quencher 406, thereby allowing the fluorophore 404 to fluoresce upon excitation.

A third signaling polynucleotide was designed based upon the aptamer sequence of SEQ ID NO: 4 described above. A 5'-T residue was appended to SEQ ID NO: 4 and the 3'-end was modified by addition of a five nucleobase segment complementary to the last five nucleobases of the 5'-end of the original aptamer sequence of SEQ ID NO: 4. Then 5'-fluorescein and 3'-DABCYL moieties were linked to produce the sequence shown below (SEQ ID NO: 7) wherein the additional five nucleobase segment is underlined along with the first five nucleobases at the 5'-end of the original aptamer sequence (not including the added the 5'-T residue).

```
                                             (SEQ ID NO: 7)
5'FluoresceinTGCAGCTAAGCAGGCGGCTCACAAAACCATTCGCATG
CGGCGCTGCDABCYL3'
```

Figure 2:
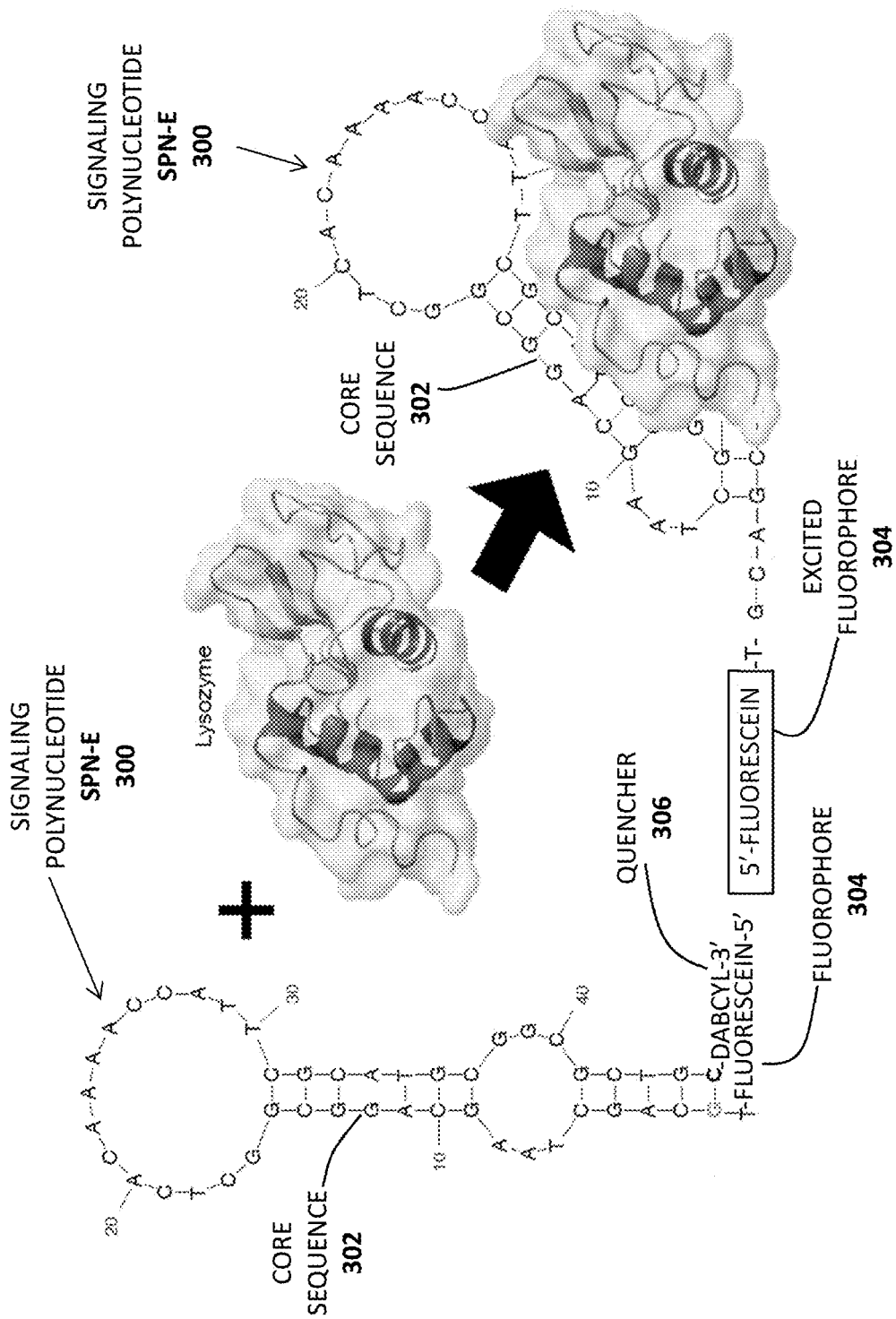
FIG. 2 shows a reaction between a detection molecule represented by a hairpin-type signaling polynucleotide SPN-E 300 (SEQ ID NO.: 7) with its target molecule lysozyme. Also shown are the aptamer core sequence 302 (SEQ ID NO.: 4), the fluorophore 304 and the quencher 306.

This signaling polynucleotide is a hairpin entity herein designated SPN-E. It will be recognized that the underlined residues at the 5'-end and the 3'-end are complementary for the purpose of forming a hairpin secondary structure as shown in the leftmost structure of FIG. 2 (core sequence 302 (SEQ ID NO.: 4). This structure brings the fluorophore 304 and quencher 306 into close proximity with each other to allow the quencher 306 to quench the fluorophore 304. The binding of the signaling polynucleotide to lysozyme can disrupt the hybridization of the two ends of the signaling polynucleotide 300 (SEQ ID NO.: 7) as shown in the rightmost structure of the core sequence 302 (SEQ ID NO.: 4), resulting in separation of the fluorophore 304 from the quencher 306, thereby activating the fluorophore 304.

Example 2: Selection and Optimization of Aptamer Polynucleotides

An in vitro screening experiment based on SELEX method was carried out and aptamers were selected against the allergen targets including egg, gluten, milk, soy, fish, peanut, cashew and crustacean, over the counter-target (combinations of the non-target proteins) and were further engineered for their capability in detecting targeted food allergens.

Experimental Plan

Various RNA libraries were used to select for binding ability in selection buffer consisting of 100 mM Tris (pH 8), 5 mM EDTA, 150 mM NaCl, 10 mM MgCl2, 0.1% SDS, 0.1% Gelatin, 1% NP-40 (Tergitol), 0.5% Deoxycholate Sodium at 23° C. A given round of selection began with incubating RNA library members in either the buffer alone (negative selection), then collecting the portion of the library that did not respond (i.e. cleave). The second part of each round (when called for) consisted of incubating the non-responsive molecules from the prior negative selection step with the full combination of non-positive targets (as the counter), or with just the selection buffer again for a second negative selection. Once again, the non-responsive (non-cleaving) molecules would be collected. The final step of each round consists of incubating the material from the previous step with the positive target (each of the allergens as appropriate) in buffer, then collecting the responsive material (i.e. cleaved RNA). Each selection round was followed by reverse transcription to generate cDNA, library amplification through PCR, and regeneration of the RNA library by transcription. After subjecting the initial library of diverse random sequences to varying consecutive rounds of selection (i.e. negative, counter and positive selections), again project-dependent, and the enriched libraries were divided into three fractions to perform the parallel assessments.

The parallel assessment of libraries enriched after rounds of negative, counter and positive selections, involves simultaneously exposing one third of the enriched library to selection buffer alone, another one-third to the counter-target complex in selection buffer, and the final one-third of the enriched library to the target allergen in buffer. Any residual RNA molecules that react indiscriminately to both target allergen and counter-targets, or that still generate a response in the absence of the target allergen were identified and discarded during further bioinformatics analysis.

The enriched RNA libraries after the parallel assessment were subjected to PAGE gel assessment. 40 pmoles of enriched library was exposed separately to either the negative (buffer only), counter target, or target allergen (e.g., milk, wheat, egg white and peanut) in selection buffer. After 5 minutes incubation at 23° C., libraries exhibiting a positive response (i.e. cleavage) material were collected, ethanol precipitated, reverse transcribed, and PCR-amplified for sequencing and bioinformatics analysis.

Materials and Methods

Targets (complexes of proteins from cashew, peanut, fish, milk, soy, gluten, egg and crustacean) were dried down, if necessary, before being combined with RNase-free water for preliminary analysis and aptamer screening. When needed, targets were pooled to produce counter-target mixture by combining appropriate amounts of the targets which were not designated as positive target for the selection. The initial aptamer library template and primers were synthesized by IDT (Coralville, Iowa) as single-stranded DNA. The library was then primer extended to provide double-stranded DNA (dsDNA) using Titanium Taq DNA polymerase from Clontech (Mountain View, Calif.).

Following the experimental plan, for a given generation of the library, RNA was transcribed from the previous dsDNA with Ampli Scribe T7 Transcription kits from Epicentre (Madison, Wis.) and purified using a 10% denaturing polyacrylamide gel electrophoresis (PAGE). The purified RNA was combined with Selection Buffer, which was then diluted to 1× concentration (100 mM Tris (pH 8), 5 mM EDTA, 150 mM NaCl, 10 mM MgCl2, 0.1% SDS, 0.1% Gelatin, 1% NP-40 (Tergitol), 0.5% Deoxycholate Sodium) for negative selection. Negative selection began with a refolding cycle, which involved heating the sample to 65° C. to denature the RNA before bringing the sample to 23° C. for the remainder of the incubation. After incubation, non-cleaved RNA was separated from cleaved RNA using 10% denaturing PAGE. Recovered non-cleaved material was combined with counter-target and buffer, target and buffer, or buffer alone depending on the selection step, incubated at 23° C., and partitioned on 10% denaturing PAGE. Recovery and another selection step was implemented if called for. cDNA was then generated from eluted post-selection library using SuperScript II Reverse Transcriptase (Life Technologies; Carlsbad, Calif.), then PCR-amplified with Titanium Taq DNA polymerase (Clontech; Mountain View, Calif.) to complete the round of selection. After several rounds of selection steps, libraries were enriched and showed that the negative cleavage amount was less than 30%, and that there was at least 5% more cleavage in the positive treatment when compared to the counter.

The initial libraries consisting of approximately $10^{14}$ random sequences was subjected to varying rounds of ribozyme-based SELEX to enrich for sequences that bind to the target allergens and to eliminated sequences that bind to the counter-targets over multiple rounds of selection. As a result, the population to be sequenced is expected to contain multiple copies of potential aptamer candidates (Van Simaeys et al., *Study of the Molecular Recognition of Aptamers Selected through Ovarian Cancer Cell-SELEX*, 2010, PLOS One, 5(11): e13770).

Sequencing and Bioinformatics

The Illumina (San Diego, Calif.) MiSeq system was implemented to sequence the aptamers after the selections using a paired-end read technique. Bioinformatics analysis of the sequencing data identified candidate aptamer molecules. The deep sequencing and subsequent data analysis reduced the traditional approach of performing a large number of selections, which may introduce error and bias due to the screening process (Schulze et al., *Probing the SELEX Process with Next-Generation Sequencing*, PLos One, 2011, 6(12): e29604).

Aptamers Candidate Selection

Sequence family construction focused on motif presence which means that a sequence's frequency in the positive target population was factored in, but places greater emphasis on the prevalence of sub-sequences in the overall population (100% match over the entire sequence not necessary to join a family). Two other factors were used to adjust the importance of motif-family size to determine candidate sequences. One factor is the presence of the sequence in the negative and counter-target population. Three libraries were collected from the parallel assessment: the positive target-exposed library, the buffer-only negative library, and the counter-target-exposed library. All libraries were analyzed to discover any sequences that have yet to be removed during a negative- or counter-selection step, but still have affinity for both the target and counter-target. A given sequence appears more frequently in the positive population than in the counter-target-exposed population, making it an attractive candidate for further testing.

The secondary structure of a given candidate sequence was also predicted using the Mfold secondary structure modeling software (Zucker, *Mfold web server for nucleic acid folding and hybridization prediction*, Nucleic Acids Res., 2003, 31 (13): 3406-3415).

A set of aptamer sequences were selected and further designed as signaling polynucleotides for detecting different food allergens, including peanut, egg white, wheat and milk. The selected aptamers are listed in Table 1. The selected aptamers for each food allergen are then further modified at either one or both of the 5' end and the 3' end to optimize the binding affinity to its targeted allergen. Modified sequences that are intended to have a fluorescein (e.g., FITC/FAM molecule) on the 5'end and a quencher on the 3' end are the signaling polynucleotides that will be tested for allergen detection as described herein.

Example 3: Total Protein Measurement

Total protein measurement is tested using Pyrogallol Red-molybdate (PRM) protein dye-binding assays. PRM is first made in a solution containing 0.156 mM pyrogallol red, 0.209 mM sodium molybdate and 50 mM Tris-HCl. A test plate is prepared by adding 20 µl/well PRM solution and the plate is dry overnight. After processing the test food matrixes, processed sample solution (400 µl) is added to each well and the protein absorbance is read immediately at 600 nm.

What is claimed is:

1. A method for determining if a food is safe to eat by a person who is allergic to peanut comprising:
   (a) obtaining a sample of the food to be tested,
   (b) processing said food sample and extracting proteins from the processed sample using an extraction buffer,
   (c) mixing the extracted proteins with a signaling polynucleotide (SPN) that comprises a nucleotide sequence presented by SEQ ID NO.: 8, and
   (d) detecting the interaction between the SPN and the peanut allergen and determining the presence or absence of the peanut allergen in the food sample.

2. The method of claim 1 wherein the nucleotide sequence or a portion of the nucleotide sequence specifically binds to the peanut allergen.

3. The method of claim 1 wherein the extraction buffer is a universal extraction buffer.

4. The method of claim 2 wherein the interaction between the SPN and the peanut allergen is detected by an enzyme-linked apta-sorbent assay (ELASA), a real-time PCR, or a fluorescence resonance energy transfer (FRET) assay.

5. A kit for detecting the presence or absence of peanut in a sample comprising: (i) a detection agent that is a nucleic acid molecule comprising a nucleotide sequence selected from the group consisting of sequences presented by SEQ ID NO. 8; (ii) one or more extraction buffers for processing the sample and extracting proteins from the sample; and (iii) an instruction that instructs a user how to use the kit.

6. The kit of claim 5 wherein the sample is a food sample.

7. The kit of claim 5 wherein the user is allergic to peanut.

* * * * *

SEQUENCE LISTING

<160> NUMBER OF SEQ ID NOS: 41

<210> SEQ ID NO 1
<211> LENGTH: 79
<212> TYPE: DNA
<213> ORGANISM: Artificial Sequence
<220> FEATURE:
<223> OTHER INFORMATION: Core Sequence of Signaling Polynucleotide

<400> SEQUENCE: 1
cgcacattcc gcttctaccg gggggggtcga gctgagtgga tgcgaatctg tgggtgggcc    60
gtaagtccgt gtgtgcgaa                                                  79

<210> SEQ ID NO 2
<211> LENGTH: 80
<212> TYPE: DNA
<213> ORGANISM: Artificial Sequence
<220> FEATURE:
<223> OTHER INFORMATION: Core Sequence of Signaling Polynucleotide
      (5'-T-modified)

<400> SEQUENCE: 2
tcgcacattc cgcttctacc gggggggtcg agctgagtgg atgcgaatct gtgggtgggc    60
cgtaagtccg tgtgtgcgaa                                                80

<210> SEQ ID NO 3
<211> LENGTH: 9
<212> TYPE: DNA
<213> ORGANISM: Artificial Sequence
<220> FEATURE:
<223> OTHER INFORMATION: Signaling Polynucleotide Linker Sequence

<400> SEQUENCE: 3 aatgtgcga                                                             9

<210> SEQ ID NO 4
<211> LENGTH: 40
<212> TYPE: DNA
<213> ORGANISM: Artificial Sequence
<220> FEATURE:
<223> OTHER INFORMATION: Core Sequence of Signaling Polynucleotide

<400> SEQUENCE: 4
gcagctaagc aggcggctca caaaaccatt cgcatgcggc                           40

<210> SEQ ID NO 5
<211> LENGTH: 41
<212> TYPE: DNA
<213> ORGANISM: Artificial Sequence
<220> FEATURE:
<223> OTHER INFORMATION: Core Sequence of Signaling Polynucleotide
      (5'-T- modified)

<400> SEQUENCE: 5
tgcagctaag caggcggctc acaaaaccat tcgcatgcgg c                         41

<210> SEQ ID NO 6
<211> LENGTH: 10
<212> TYPE: DNA
<213> ORGANISM: Artificial Sequence
<220> FEATURE:
<223> OTHER INFORMATION: Signaling Polynucleotide Linker Sequence

<400> SEQUENCE: 6
cttagctgca                                                            10

<210> SEQ ID NO 7
<211> LENGTH: 46
<212> TYPE: DNA
<213> ORGANISM: Artificial Sequence
<220> FEATURE:
<223> OTHER INFORMATION: Core sequence of Signaling Polynucleotide

<400> SEQUENCE: 7
tgcagctaag caggcggctc acaaaaccat tcgcatgcgg cgctgc         46

<210> SEQ ID NO 8
<211> LENGTH: 83
<212> TYPE: DNA
<213> ORGANISM: Artificial Sequence
<220> FEATURE:
<223> OTHER INFORMATION: Aptamer: Core Sequence of signal polynucleotide

<400> SEQUENCE: 8
ttcgcgcaca ttccgcttct accgggggg tcgagctgag tggatgcgaa tctgtgggtg    60
ggccgtaagt ccgtgtgtgc gaa                                          83

<210> SEQ ID NO 9
<211> LENGTH: 89
<212> TYPE: DNA
<213> ORGANISM: Artificial Sequence
<220> FEATURE:
<223> OTHER INFORMATION: Aptamer: Core sequence of signal polynucleotide

<400> SEQUENCE: 9
tcgcacattc cgcttctacc gggggggtcg agctgagtgg atgcgaatct gtgggtgggc   60
cgtaagtccg tgtgtgcgaa aatgtgcga                                    89

<210> SEQ ID NO 10
<211> LENGTH: 87
<212> TYPE: DNA
<213> ORGANISM: Artificial Sequence
<220> FEATURE:
<223> OTHER INFORMATION: Aptamer: Core Sequence of signal polynucleotide

<400> SEQUENCE: 10
tcgcacattc cgcttctacc gggggggtcg agctgagtgg atgcgaatct gtgggtgggc   60
cgtaagtccg tgtgtgcgaa tgtgcga                                      87

<210> SEQ ID NO 11
<211> LENGTH: 49
<212> TYPE: DNA
<213> ORGANISM: Artificial Sequence
<220> FEATURE:
<223> OTHER INFORMATION: Aptamer: Core sequence of signal polynucleotide

<400> SEQUENCE: 11
tggcagctaa gcaggcggct cacaaaacca ttcgcatgcg gctgttcca      49

<210> SEQ ID NO 12
<211> LENGTH: 47
<212> TYPE: DNA
<213> ORGANISM: Artificial Sequence
<220> FEATURE:
<223> OTHER INFORMATION: Aptamer: Core sequence of signal polynucleotide

<400> SEQUENCE: 12
tgcagctaag caggcggctc acaaaaccat tcgcatgcgg cgctgca        47

<210> SEQ ID NO 13
<211> LENGTH: 45
<212> TYPE: DNA
<213> ORGANISM: Artificial Sequence
<220> FEATURE:
<223> OTHER INFORMATION: Aptamer: Core sequence of signal polynucleotide

<400> SEQUENCE: 13
tgcagctaag caggcggctc acaaaaccat tcgcatgcgg ctgca            45

<210> SEQ ID NO 14
<211> LENGTH: 45
<212> TYPE: DNA
<213> ORGANISM: Artificial Sequence
<220> FEATURE:
<223> OTHER INFORMATION: Aptamer: Core sequence of signal polynucleotide

<400> SEQUENCE: 14
gcagctaagc aggcggctca caaaaccatt cgcatgcggc gctgc            45

<210> SEQ ID NO 15
<211> LENGTH: 48
<212> TYPE: DNA
<213> ORGANISM: Artificial Sequence
<220> FEATURE:
<223> OTHER INFORMATION: Aptamer: Core sequence of signal polynucleotide

<400> SEQUENCE: 15
tttcccagtc tcccgtttac cgcgcctaca catgtctgaa tgccgaaa         48

<210> SEQ ID NO 16
<211> LENGTH: 111
<212> TYPE: DNA
<213> ORGANISM: Artificial Sequence
<220> FEATURE:
<223> OTHER INFORMATION: Aptamer: Core sequence of signal polynucleotide

<400> SEQUENCE: 16
tcgaaaagct gcagctgcaa ccatttccgc agccgcaact accatatccg cagccgcaac    60
taccatatcc gcagccgcaa ctaccatatc cgcagcggca accattttcg a            111

<210> SEQ ID NO 17
<211> LENGTH: 56
<212> TYPE: DNA
<213> ORGANISM: Artificial Sequence
<220> FEATURE:
<223> OTHER INFORMATION: Aptamer: Core sequence of signal polynucleotide

<400> SEQUENCE: 17
aacaaactac taactaggta agatcacgca gcactaaacg acgtagttgc catgtt        56

<210> SEQ ID NO 18
<211> LENGTH: 53
<212> TYPE: DNA
<213> ORGANISM: Artificial Sequence
<220> FEATURE:
<223> OTHER INFORMATION: Aptamer: Core sequence of signal polynucleotide

<400> SEQUENCE: 18
tggcaaacta ctaactaggt aagatcacgc agcactaaac gacgtagttg cca           53

<210> SEQ ID NO 19
<211> LENGTH: 54
<212> TYPE: DNA
<213> ORGANISM: Artificial Sequence

```
<220> FEATURE:
<223> OTHER INFORMATION: Aptamer: Core sequence of signal polynucleotide

<400> SEQUENCE: 19
ttggaaacta ctaactaggt aagatcacgc agcactaaac gacgtagttg ccaa            54

<210> SEQ ID NO 20
<211> LENGTH: 118
<212> TYPE: DNA
<213> ORGANISM: Artificial Sequence
<220> FEATURE:
<223> OTHER INFORMATION: Aptamer: Core sequence of signal polynucleotide

<400> SEQUENCE: 20
ccgagctaaa tgctgcagct gcaaccattt ccgcagccgc aactaccata tccgcagccg      60
caactaccat atccgcagcc gcaactacca tatccgcagc ggcaaccatt tagctcgg       118

<210> SEQ ID NO 21
<211> LENGTH: 112
<212> TYPE: DNA
<213> ORGANISM: Artificial Sequence
<220> FEATURE:
<223> OTHER INFORMATION: Aptamer: Core sequence of signal polynucleotide

<400> SEQUENCE: 21
ccgaaaatgc tgcagctgca accatttccg cagccgcaac taccatatcc gcagccgcaa      60
ctaccatatc cgcagccgca actaccatat ccgcagcggc aaccattttc gg             112

<210> SEQ ID NO 22
<211> LENGTH: 46
<212> TYPE: DNA
<213> ORGANISM: Artificial Sequence
<220> FEATURE:
<223> OTHER INFORMATION: Aptamer: Core sequence of signal polynucleotide

<400> SEQUENCE: 22
ccagtctccc gtttaccgcg cctacacatg tctgaatgcc gactgg                     46

<210> SEQ ID NO 23
<211> LENGTH: 44
<212> TYPE: DNA
<213> ORGANISM: Artificial Sequence
<220> FEATURE:
<223> OTHER INFORMATION: Aptamer: Core sequence of signal polynucleotide

<400> SEQUENCE: 23
ggcaccagtc tcccgtttac cgcgcctaca catgtctgaa tgcc                       44

<210> SEQ ID NO 24
<211> LENGTH: 53
<212> TYPE: RNA
<213> ORGANISM: Artificial Sequence
<220> FEATURE:
<223> OTHER INFORMATION: Aptamer: Core sequence of signal polynucleotide

<400> SEQUENCE: 24
augagcuugg ucaccuuucc ugacauuaac acaggcgaaa cggugaaagc cgu             53

<210> SEQ ID NO 25
<211> LENGTH: 55
<212> TYPE: RNA
<213> ORGANISM: Artificial Sequence
<220> FEATURE:
<223> OTHER INFORMATION: Aptamer: Core sequence of signal polynucleotide
```

<400> SEQUENCE: 25
caugaguuuu cccgauacgg cuacgaauug cgacaacgaa acggugaaag ccgug      55

<210> SEQ ID NO 26
<211> LENGTH: 52
<212> TYPE: RNA
<213> ORGANISM: Artificial Sequence
<220> FEATURE:
<223> OTHER INFORMATION: Aptamer; Core sequence of signal polynucleotide

<400> SEQUENCE: 26
ugaguuuucc cgauacggcu acgaauugcg acaacgaaac ggugaaagcc ca         52

<210> SEQ ID NO 27
<211> LENGTH: 92
<212> TYPE: DNA
<213> ORGANISM: Artificial Sequence
<220> FEATURE:
<223> OTHER INFORMATION: Aptamer

<400> SEQUENCE: 27
gctgacacag caggttggtg ggggtggctt ccagttgggt tgacaatacg tagggacacg    60
aagtccaacc acgagtcgag caatctcgaa at                                 92

<210> SEQ ID NO 28
<211> LENGTH: 11
<212> TYPE: DNA
<213> ORGANISM: Artificial Sequence
<220> FEATURE:
<223> OTHER INFORMATION: Aptamer: Synthetic polynucleotide

<400> SEQUENCE: 28
ggtgggggtg g      11

<210> SEQ ID NO 29
<211> LENGTH: 81
<212> TYPE: DNA
<213> ORGANISM: Artificial Sequence
<220> FEATURE:
<223> OTHER INFORMATION: Aptamer: Synthetic polynucleotide

<400> SEQUENCE: 29
cttctgcccg cctccttccg ttaatggggg atctcgcggc cgttcttgtt gcttatacag    60
gagacgagat aggcggacac t                                             81

<210> SEQ ID NO 30
<211> LENGTH: 80
<212> TYPE: DNA
<213> ORGANISM: Artificial Sequence
<220> FEATURE:
<223> OTHER INFORMATION: Aptamer: Synthetic polynucleotide

<400> SEQUENCE: 30
gggaatggat ccacatctac gaattcatca gggctaaaga gtgcagagtt acttagttca    60
ctgcagactt gacgaagctt                                               80

<210> SEQ ID NO 31
<211> LENGTH: 80
<212> TYPE: DNA
<213> ORGANISM: Artificial Sequence
<220> FEATURE:
<223> OTHER INFORMATION: Aptamer: Synthetic polynucleotide

<400> SEQUENCE: 31

```
agcagcacag aggtcagatg gcaggtaagc aggcggctca caaaaccatt cgcatgcggc    60
cctatgcgtg ctaccgtgaa                                                80
```

<210> SEQ ID NO 32
<211> LENGTH: 95
<212> TYPE: RNA
<213> ORGANISM: Artificial Sequence
<220> FEATURE:
<223> OTHER INFORMATION: Aptamer: Synthetic polynucleotide

<400> SEQUENCE: 32

```
ggaccucggc gaaagcuaac gucucauggc uaaauugcca uguugcuaca aaugauauga    60
cuagagaggu uaggugccuc gugaugucca gucgc                               95
```

<210> SEQ ID NO 33
<211> LENGTH: 42
<212> TYPE: RNA
<213> ORGANISM: Artificial Sequence
<220> FEATURE:
<223> OTHER INFORMATION: Aptamer: Synthetic polynucleotide

<400> SEQUENCE: 33

```
uagugugaga gccgugagug aaaggccgcg acaaagaucg ga                       42
```

<210> SEQ ID NO 34
<211> LENGTH: 90
<212> TYPE: RNA
<213> ORGANISM: Artificial Sequence
<220> FEATURE:
<223> OTHER INFORMATION: Aptamer: Synthetic polynucleotide

<400> SEQUENCE: 34

```
ggguucacug cagacuugac gaagcuugag agaugccccc ugaugugcau ucuuguugug    60
uugcggcaau ggauccacau cuacgaauuc                                     90
```

<210> SEQ ID NO 35
<211> LENGTH: 47
<212> TYPE: DNA
<213> ORGANISM: Artificial Sequence
<220> FEATURE:
<223> OTHER INFORMATION: Aptamer: Synthetic polynucleotide

<400> SEQUENCE: 35

```
atccatgggg cggagatgag ggggaggagg gcgggtaccc ggttgat                  47
```

<210> SEQ ID NO 36
<211> LENGTH: 60
<212> TYPE: DNA
<213> ORGANISM: Artificial Sequence
<220> FEATURE:
<223> OTHER INFORMATION: Aptamer: Synthetic polynucleotide

<400> SEQUENCE: 36

```
ggagaccgta ccatctgttc gtggaagcgc tttgctcgtc cattagcctt gtgctcgtgc    60
```

<210> SEQ ID NO 37
<211> LENGTH: 64
<212> TYPE: RNA
<213> ORGANISM: Artificial Sequence
<220> FEATURE:
<223> OTHER INFORMATION: Aptamer: Synthetic nucleic acid

<400> SEQUENCE: 37

```
ggucuuccu ggacugucga aaauucagua ucgggagguu acguauuugg uuuauagaua    60
guaa                                                               64

<210> SEQ ID NO 38
<211> LENGTH: 124
<212> TYPE: DNA
<213> ORGANISM: Artificial Sequence
<220> FEATURE:
<223> OTHER INFORMATION: Aptamer: Synthetic polynucleotide

<400> SEQUENCE: 38
cacggatcct gacaaggatg tgtgcgttgt cgagacctgc gaccggaaca ctacactgtg    60
tgggatggat ttctttacag ttgtgtgcag ctccgtccga ctcttcctag cggttcgatc   120
aaga                                                               124

<210> SEQ ID NO 39
<211> LENGTH: 78
<212> TYPE: DNA
<213> ORGANISM: Artificial Sequence
<220> FEATURE:
<223> OTHER INFORMATION: Aptamer: Synthetic polynucleotide

<400> SEQUENCE: 39
ggtattgagg gtcgcatcca ctggtcgttg ttgtctgttg tctgttatgt tgtttcgtga    60
tggctctaac tctcctct                                                 78

<210> SEQ ID NO 40
<211> LENGTH: 99
<212> TYPE: RNA
<213> ORGANISM: Artificial Sequence
<220> FEATURE:
<223> OTHER INFORMATION: Aptamer: Synthetic polynucleotide

<400> SEQUENCE: 40
ggauguccag ucgcuugcaa ugcccuuuua gacccugaug aggaucaucg gacuuugucc    60
uguggaguaa gaucgcgaaa cggugaaagc cguaggucu                          99

<210> SEQ ID NO 41
<211> LENGTH: 22
<212> TYPE: DNA
<213> ORGANISM: Artificial Sequence
<220> FEATURE:
<223> OTHER INFORMATION: Aptamer: Synthetic polynucleotide

<400> SEQUENCE: 41
ttctttcttc cccttgtttg tt                                            22
```